(12) United States Patent
Poncelet et al.

(10) Patent No.: US 8,853,406 B2
(45) Date of Patent: Oct. 7, 2014

(54) SUBSTITUTED PHENYLENEDIAMINES AS INHIBITORS OF THE INTERACTION BETWEEN MDM2 AND P53

(75) Inventors: Alain Philippe Poncelet, Le Manoir sur Seine (FR); Bruno Schoentjes, Bois-Guillaume (FR); Pierre-Henri Storck, Ramsgate (GB); Virginie Sophie Poncelet, Le Manoir sur Seine (FR); Carina Leys, Stabroek (BE)

(73) Assignee: Janssen Pharmaceutica NV, Beerse (BE)

( * ) Notice: Subject to any disclaimer, the term of this patent is extended or adjusted under 35 U.S.C. 154(b) by 307 days.

(21) Appl. No.: 12/672,381

(22) PCT Filed: Aug. 5, 2008

(86) PCT No.: PCT/EP2008/060291
§ 371 (c)(1),
(2), (4) Date: Feb. 5, 2010

(87) PCT Pub. No.: WO2009/019274
PCT Pub. Date: Feb. 12, 2009

(65) Prior Publication Data
US 2011/0130418 A1    Jun. 2, 2011

Related U.S. Application Data

(60) Provisional application No. 60/974,207, filed on Sep. 21, 2007.

(30) Foreign Application Priority Data

Aug. 6, 2007 (EP) .................................. 07113878

(51) Int. Cl.
*C07D 221/04* (2006.01)
*A61K 31/435* (2006.01)
*C07D 401/12* (2006.01)

(52) U.S. Cl.
CPC .................................. *C07D 401/12* (2013.01)
USPC ......................................... 546/183; 514/299

(58) Field of Classification Search
USPC ......................................... 546/183; 514/299
See application file for complete search history.

(56) References Cited

U.S. PATENT DOCUMENTS 7,122,547 B1   10/2006   Huth et al.
7,834,016 B2 *  11/2010   Lacrampe et al. ....... 514/252.06

FOREIGN PATENT DOCUMENTS

| EP | 1379239 | 9/2007 |
|---|---|---|
| EP | 1519932 | 10/2007 |
| EP | 1458380 | 3/2008 |
| EP | 1443937 | 6/2008 |
| EP | 1317443 | 1/2009 |
| EP | 1809622 | 7/2010 |
| JP | 11130750 | 5/1999 |
| WO | WO 0015357 | 3/2000 |
| WO | WO 0027819 | 5/2000 |
| WO | WO 0032175 | 6/2000 |
| WO | WO 0142224 | 6/2001 |
| WO | WO 03040402 | 5/2003 |
| WO | WO 2006/032631 | 3/2006 |

OTHER PUBLICATIONS

Matthew L. Peterson et. al. "Expanding the Scope of Crystal Form Evaluation in Pharmaceutical Science" Journal of Pharmacy & Pharmaceutical Science 2006 (9(3):317-326.*
Vousden, K.H. "p53: Death Star", *Cell*, vol. 103, Nov. 22, 2000, pp. 691-694.
United Kingdom Committee on Cancer Research, Guidelines for the Welfare of Animals in Experimental Neoplasia (Second Edition). *British Journal of Cancer*, (1996), 77 (1), pp. 1-10.
Filinger, E. J. "Effect of a Reserpine-like Agent on the Release and Metabolism [3H] NA in Cell Bodies and Terminals", *Gen. Pharmac.*, vol. 25, No. 5, (1994) pp. 1039-1043.
Colzi, A. et al. "Monoamine Oxidase—A Inhibitors and Dopamine Metabolism in Rat Caudatus: Evidence that an Increased Cytosolic Level of Dopamine Displaces Reversible Monoamine Oxidase—A Inhibitors In Vivo", *The Journal of Pharmacology and Experimental Therapeutics*, (1993), vol. 265, No. 1, pp. 103-111.
Colpaert, F.C.et al., "A Critical Study onRO-4-1284 Antagonism in Mice", *Arch. Int. Pharmacodyn.*, (1975), 215, pp. 40-90.
Blattner, C. et al., "Hypophosphorylation of Mdm2 Augments p53 Stability", *Molecular and Cellular Biology*, vol. 22, No. 17, (Sep. 2002), pp. 6170-6182.

* cited by examiner

*Primary Examiner* — David K O Dell

(57) ABSTRACT

The present invention provides compounds of formula (I), their use as an inhibitor of a p53-MDM2 interaction as well as pharmaceutical compositions comprising said compounds of formula (I).

(I)

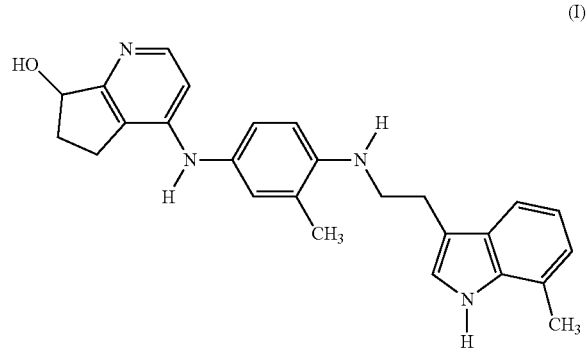

9 Claims, 7 Drawing Sheets

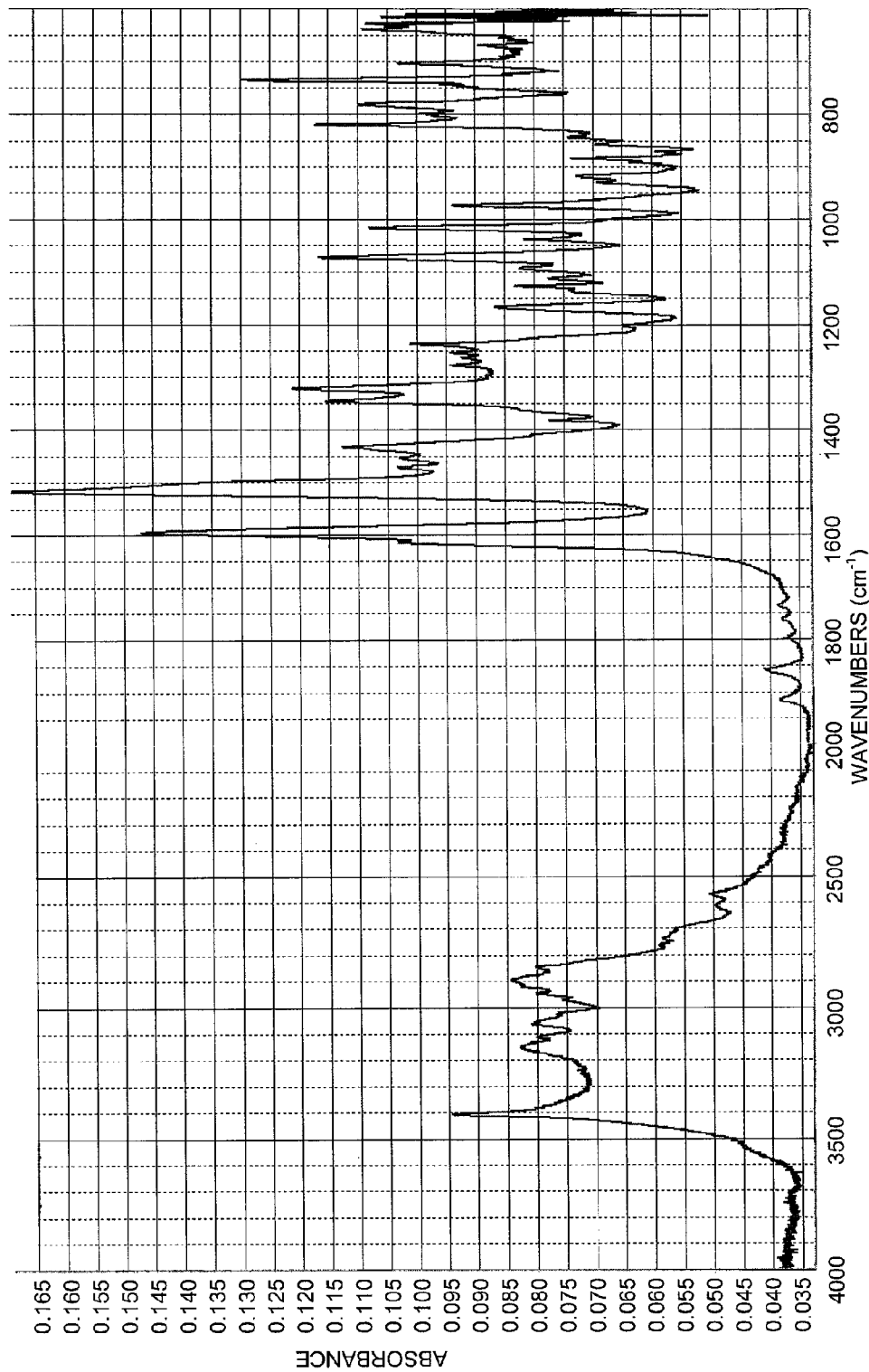
Figure 1: Infrared spectrometry: Form I

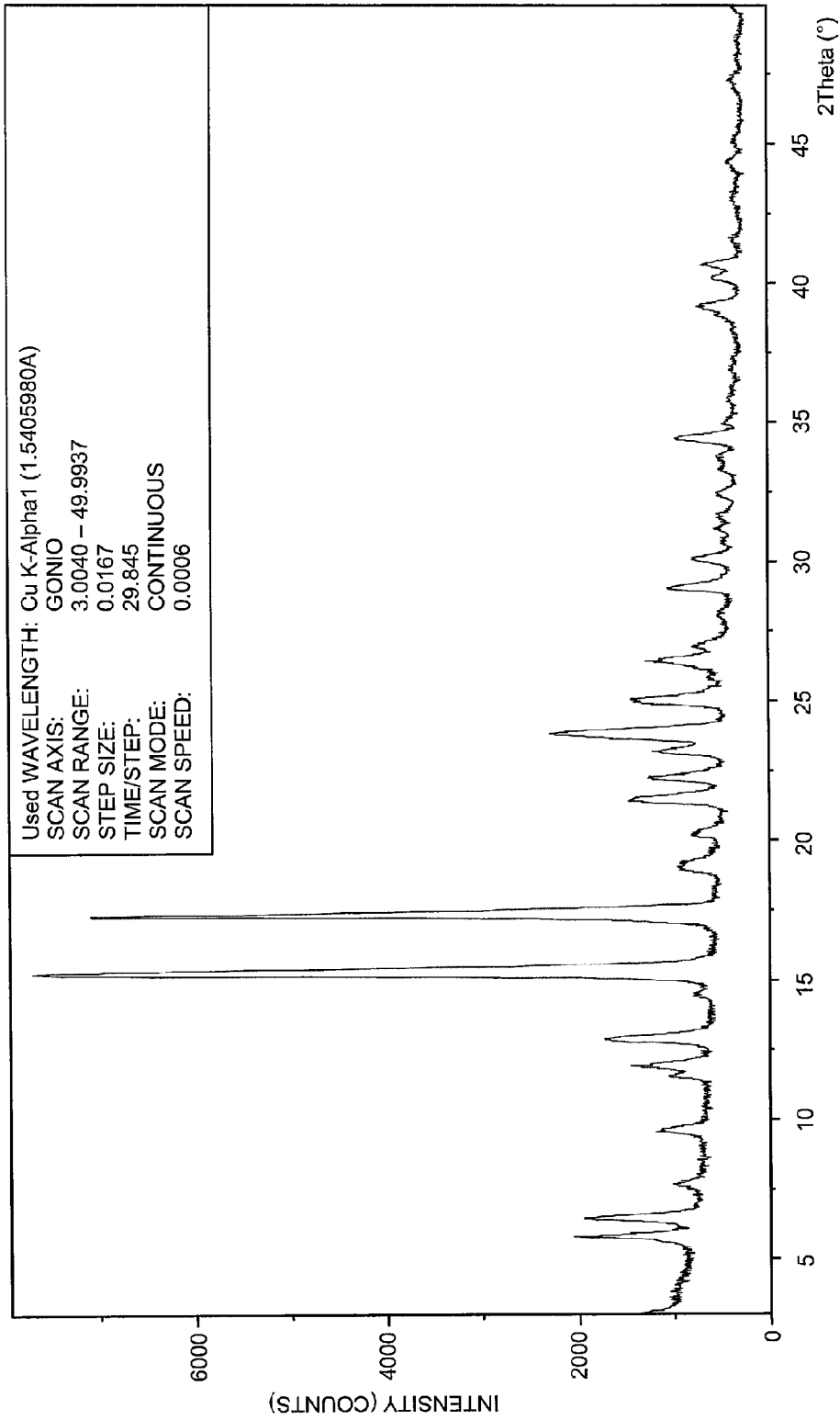
Figure 2: Powder XRD: Form I

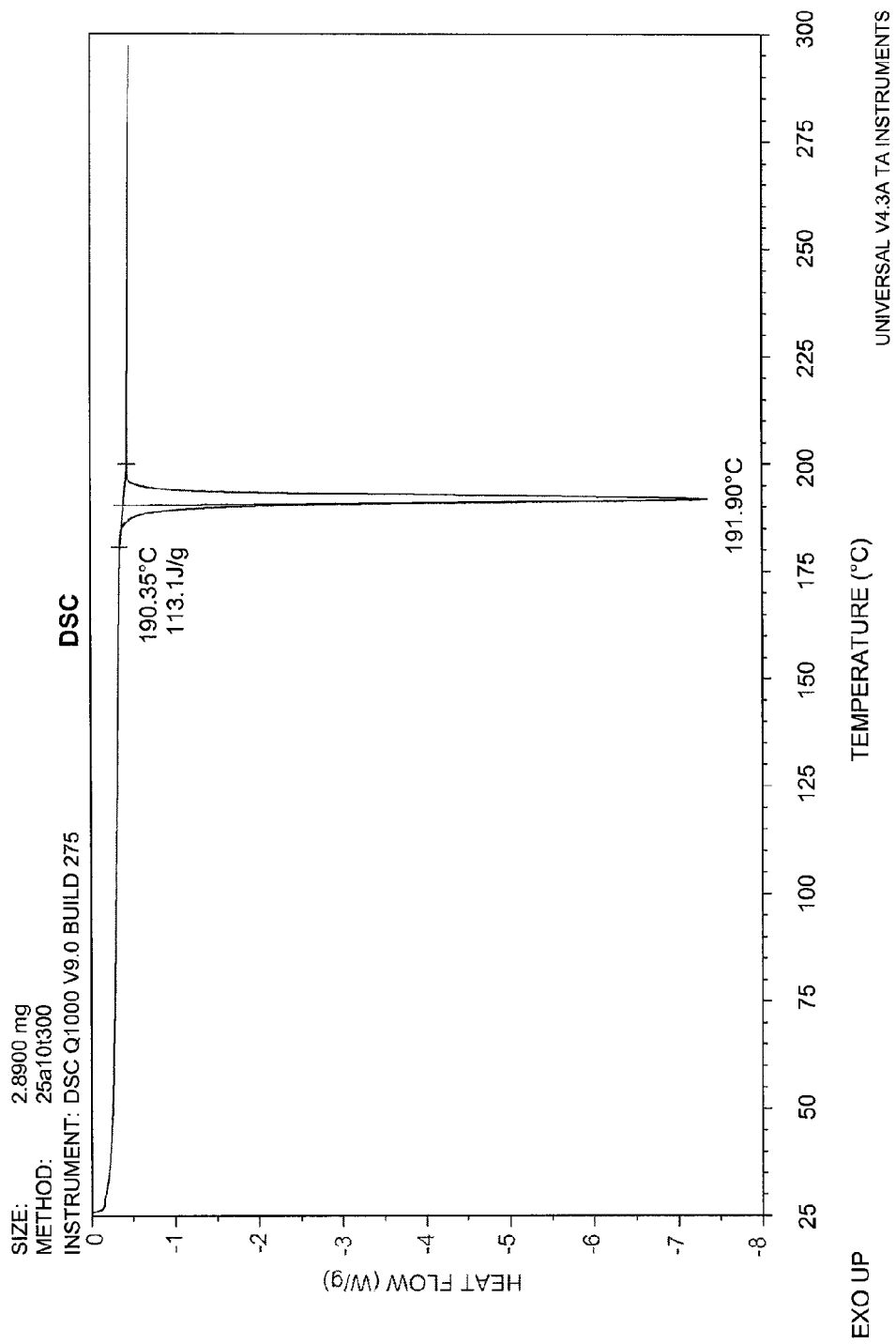
Figure 3: DSC: Form I

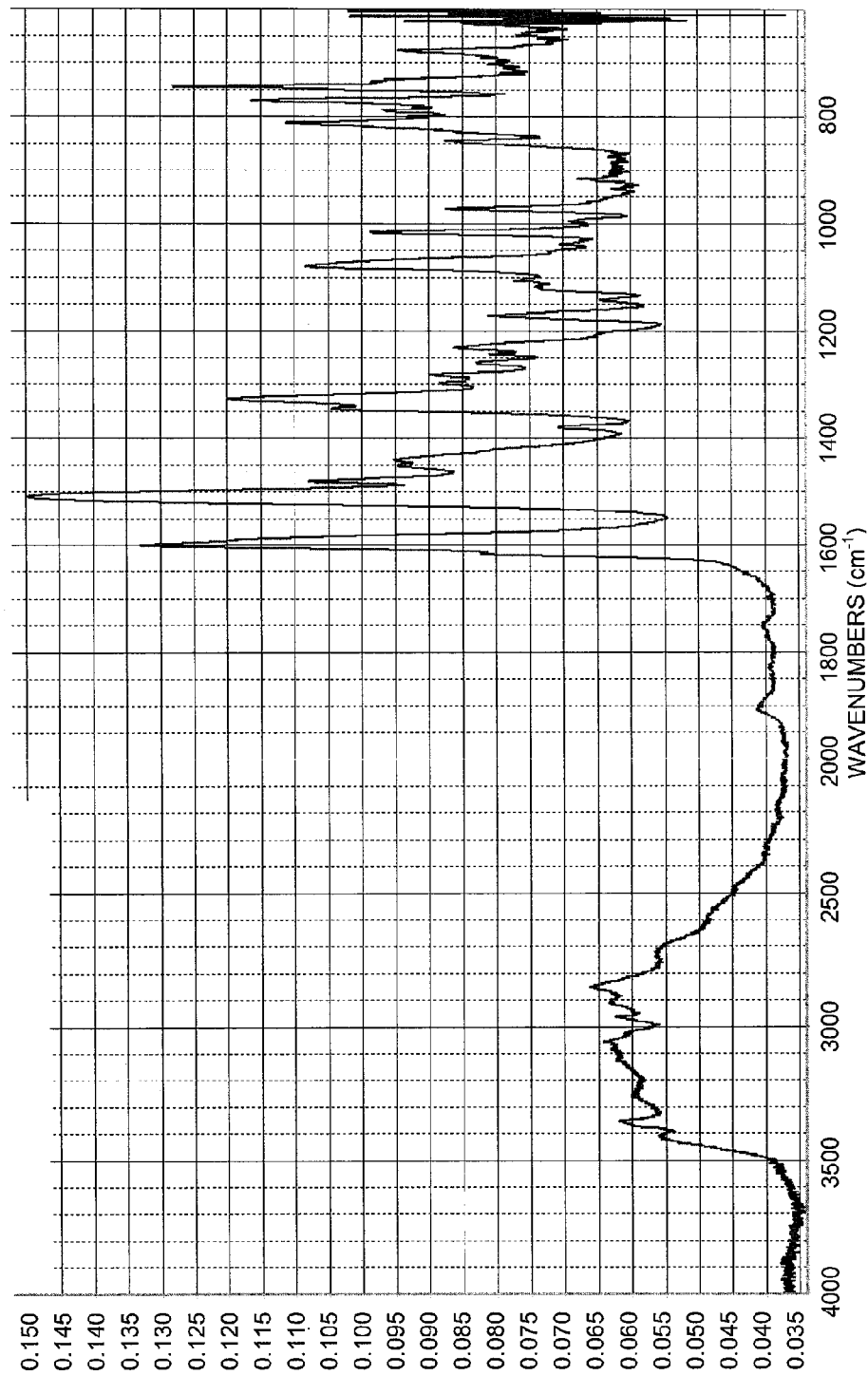
Figure 4: Infrared spectrometry: Form II

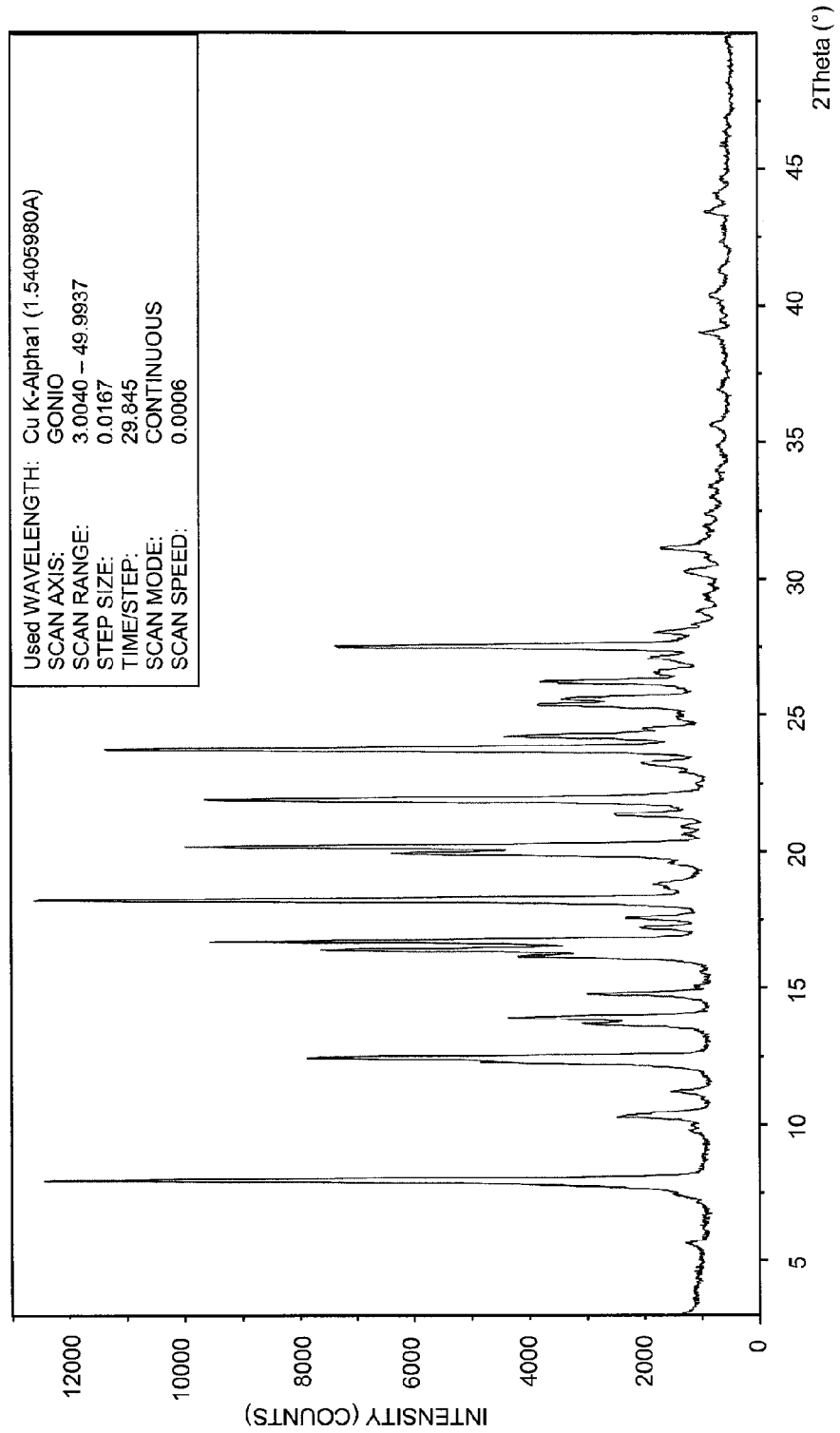
Figure 5: Powder XRD: Form II

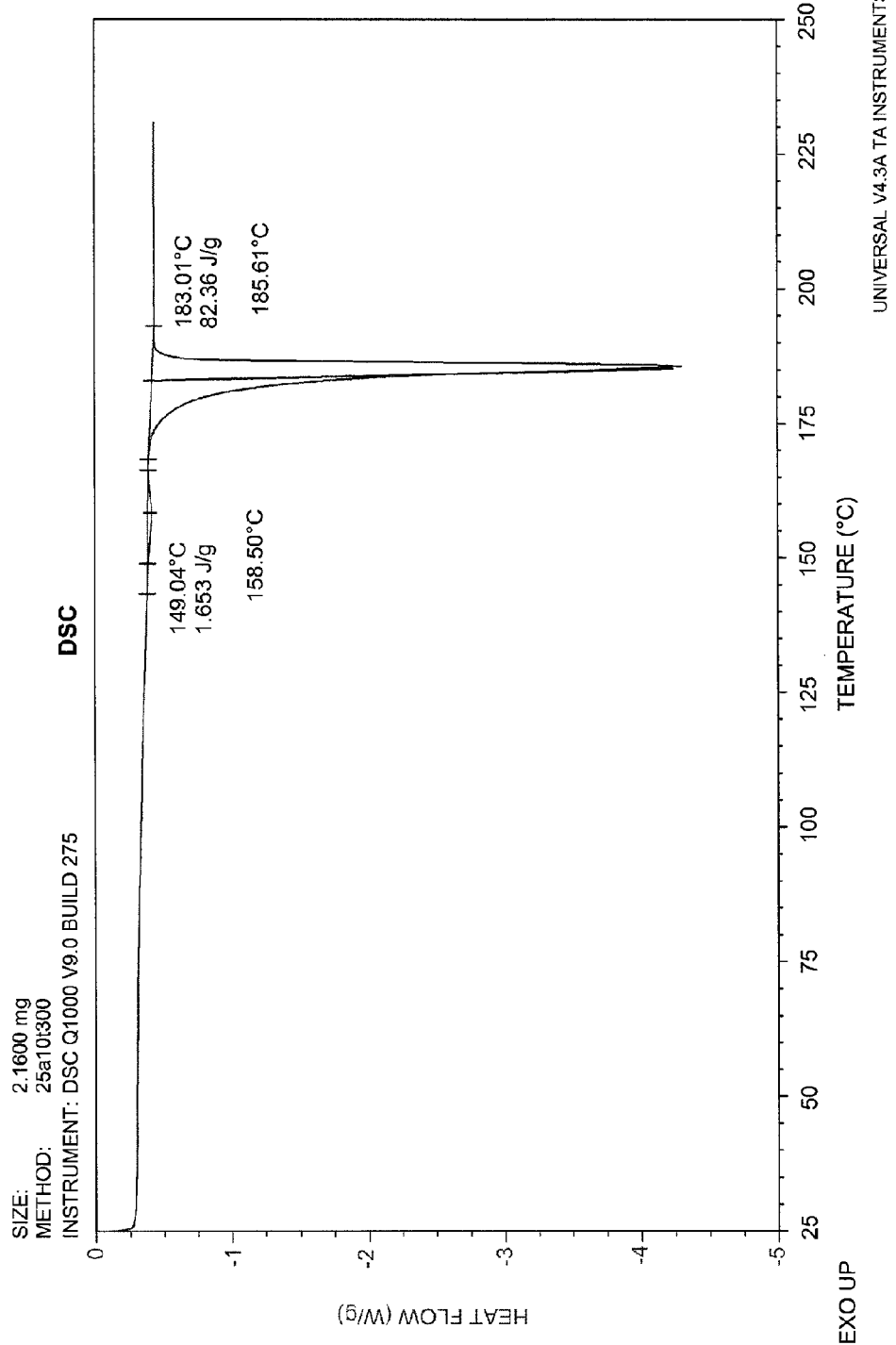
Figure 6: DSC: Form II

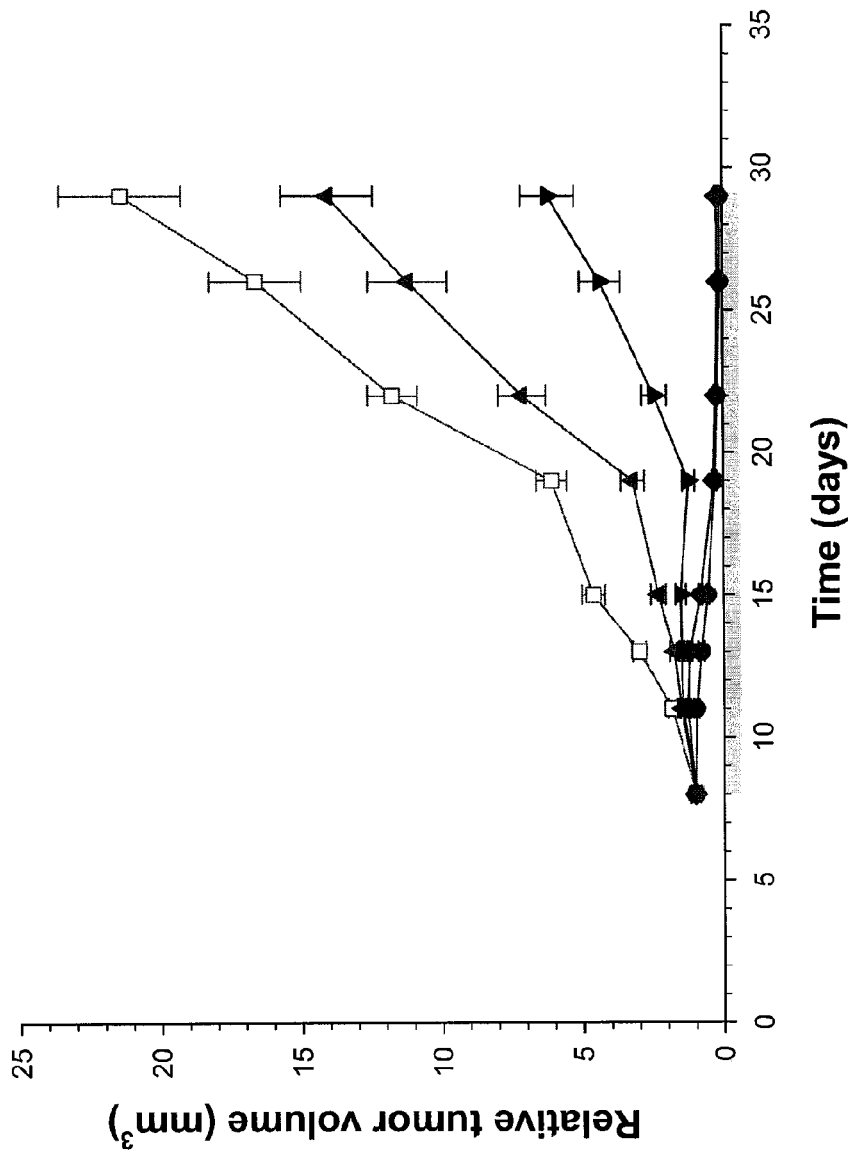
Figure 7: Antitumoral effect of compound No. 1 in U87 Glioblastoma Xenograft Tumors in NMRI Nude Mice

SUBSTITUTED PHENYLENEDIAMINES AS INHIBITORS OF THE INTERACTION BETWEEN MDM2 AND P53

CROSS REFERENCE TO RELATED APPLICATIONS

This application is the national stage of PCT Application No. PCT/EP2008/060291 filed Aug. 5, 2008, which claims priority from European Patent Application No. 07113878.8, filed Aug. 6, 2007 and U.S. Patent Application No. 60/974,207 filed Sep. 21, 2007, the entire disclosures of which are hereby incorporated in their entirety.

FIELD OF THE INVENTION

The present invention relates to compounds and compositions containing said compounds acting as inhibitors of the interaction between MDM2 and p53, in particular modulators of the MDM2-proteasome interaction. Moreover, the present invention provides processes for the preparation of the disclosed inhibitors, compositions comprising them and methods of using them, for instance as a medicine.

p53 is a tumour suppressor protein which plays a pivotal role in the regulation of the balance between cell proliferation and cell growth arrest/apoptosis. Under normal conditions the half life of p53 is very short and consequently the level of p53 in cells is low. However, in response to cellular DNA damage or cellular stress (e.g. oncogene activation, telomere erosion, hypoxia), levels of p53 increase. This increase in p53 levels leads to the activation of the transcription of a number of genes which drives the cell into either growth arrest or into the processes of apoptosis. Thus, an important function of p53 is to prevent the uncontrolled proliferation of damaged cells and thus protect the organism from the development of cancer.

MDM2 is a key negative regulator of p53 function. It forms a negative autoregulatory loop by binding to the amino terminal transactivation domain of p53 and thus MDM2 both inhibits the ability of p53 to activate transcription and targets p53 for proteolytic degradation. Under normal conditions this regulatory loop is responsible for maintaining the low levels of p53. However, in tumours with wild-type p53, the equilibrium concentration of active p53 can be increased by antagonising the interaction between MDM2 and p53. Other activities of MDM2 are also required for p53 degradation, as evidenced by the accumulation of ubiquitylated p53 when phosphorylation in the central domain of HDM2 is abrogated (Blattner et al., Hypophosphorylation of Mdm2 augments p53 stability. (2002) *Mol. Cell. Biol.*, 22, 6170-6182). The association of HDM2 with different subunits of the 26S proteasome such as S4, S5a, S6a and S6b ($3^{rd}$ Mdm2 workshop, September 2005 in Constance, Germany) might play a key role in this process. Thus, p53 concentrations can also be increased by modulating the MDM2-proteasome interaction. This will result in restoration of the p53-mediated pro-apoptotic and anti-proliferative effects in such tumour cells. MDM2 antagonists might even exhibit anti-proliferative effects in tumour cells that are devoid of functional p53.

This positions the HDM2 protein as an attractive target for the development of anti-cancer therapy.

MDM2 is a cellular proto-oncogene. Over-expression of MDM2 has been observed in a range of cancers. MDM2 is over-expressed in a variety of tumours due to gene amplification or increased transcription or translation. The mechanism by which MDM2 amplification promotes tumourigenesis is at least in part related to its interaction with p53. In cells over-expressing MDM2 the protective function of p53 is blocked and thus cells are unable to respond to DNA damage or cellular stress by increasing p53 levels, leading to cell growth arrest and/or apoptosis. Thus after DNA damage and/or cellular stress, cells over-expressing MDM2 are free to continue to proliferate and assume a tumorigenic phenotype. Under these conditions disruption of the interaction of p53 and MDM2 would release the p53 and thus allow normal signals of growth arrest and/or apoptosis to function.

MDM2 may also have separate functions in addition to inhibition of p53. The number of MDM2 substrates is rapidly expanding. For example, it has been shown that MDM2 interacts directly with the pRb-regulated transcription factor E2F1/DP1. This interaction could be crucial for the p53-independent oncogenic activities of MDM2. A domain of E2F1 shows striking similarity to the MDM2-binding domain of p53. Since the interactions of MDM2 with both p53 and E2F1 locate to the same binding site on MDM2, it can be expected that MDM2/p53 antagonists will not only activate cellular p53 but also modulate E2F1 activities, which are commonly deregulated in tumour cells. Other key examples of MDM2 substrates include p63, p73, $p21^{waf1,cip1}$.

Also the therapeutic effectiveness of DNA damaging agents currently used (chemotherapy and radiotherapy), may be limited through the negative regulation of p53 by MDM2. Thus if the MDM2 feed-back inhibition of p53 is interrupted, an increase in functional p53 levels will increase the therapeutic effectiveness of such agents by restoring the wild-type p53 function that leads to apoptosis and/or reversing of p53-associated drug resistance. It was demonstrated that combining MDM2 inhibition and DNA-damaging treatments in vivo led to synergistic anti-tumour effects (Vousden K. H., Cell, Vol. 103, 691-694, 2000).

Thus disruption of the interaction of MDM2 and p53 offers an approach for therapeutic intervention in tumours with wild-type or mutant p53, might even exhibit anti-proliferative effects in tumour cells that are devoid of functional p53 and furthermore can sensitise tumorigenic cells for chemotherapy and radiotherapy.

BACKGROUND OF THE INVENTION

JP 11130750, published on 18 May 1999, describes amongst others, substituted phenylaminocarbonylindolyl derivatives as 5-HT receptor antagonists.

EP1129074, published on 18 May 2000, describes anthranilic acid amides as inhibitors of vascular endothelial growth factor receptors (VEGFR) and useful in the treatment of angiogenic disorders.

WO01/42224, published on 14 Jun. 2001, provides carboxyamido derivatives for the treatment of Alzheimer disease.

EP1317443, published on 21 Mar. 2002, discloses tricyclic tert-amine derivatives, useful as chemokine receptor CXCR4 or CCR5 modulators for treating human immunodeficiency virus and feline immunodeficiency virus.

EP1379239, published on 10 Oct. 2002, discloses N-(2-arylethyl)benzylamines as antagonists of the 5-$HT_6$ receptor.

WO00/15357, published on 23 Mar. 2000, provides piperazine-4-phenyl derivatives as inhibitors of the interaction between MDM2 and p53. EP1137418, published on 8 Jun. 2000, provides tricyclic compounds for restoring conformational stability of a protein of the p53 family.

WO03/040402, published on 15 May 2003, provides compounds that inhibit the interactions between proteins, such as the interaction between MDM2 and p53.

EP1443937, published on 22 May 2003, describes substituted 1,4-benzodiazepines and the uses thereof as inhibitors of the MDM2-p53 interactions.

EP1458380, published on 26 Jun. 2003, provides cis-2,4,5-triphenyl-imidazolones that inhibit the interaction of MDM2 protein with p53-like peptides and have antiproliferative activity.

EP1519932, published on 15 Jan. 2004, discloses bisarylsulfonamide compounds that bind to MDM2 and can be used in cancer therapy.

EP1809622, published on 30 Mar. 2006, discloses inhibitors of the interaction between MDM2 and p53.

There is a need for effective small molecules that inhibit the interactions between MDM2 and p53, have potent inhibitory effect against tumor cell growth, have a broad safety profile and less undesired side effects.

The compounds of the present invention show excellent in-vitro activity. They have low affinity for the P450 enzymes which reduces the risk of adverse drug-drug interaction allowing for a wider safety margin. Moreover, the compounds of the present invention show excellent in vivo anti tumor effects while having less in vivo drug induced neurological effects.

DESCRIPTION OF THE FIGURES

FIG. 1 is an Infrared (IR) spectrum representation of Form I

FIG. 2 is an X-ray powder Diffraction (XRPD) pattern representation of Form I FIG. 3 is a Differential Scanning calorimetry (DSC) curve of Form I FIG. 4 is an IR spectrum representation of Form II FIG. 5 is an XRPD pattern representation of Form II FIG. 6 is a DSC curve of Form II FIG. 7 is the Antitumoral effect of compound No. 1 in U87 Glioblastoma Xenograft Tumors in NMRI Nude mice:

On day 0, male NMRI Nude mice were inoculated with a single subcutaneous injection into the inguinal region with human U87 Glioblastoma tumor cells (106 cells/mouse). On day 8, mice were treated p.o. with vehicle (control group; 10% hydroxypropyl-β-cyclodextrin (□)) or vehicle containing Co No. 1 at either 2.5 mg/kg (▲), 5 mg/kg (▼), 10 mg/kg (♦) or 20 mg/kg (●) for 21 days (QD×21). Subcutaneous tumor volumes and body weights were measured twice weekly, until end of study and results represented as relative tumor volumes (mm³). Dosing period indicated under x-axis.

DESCRIPTION OF THE INVENTION

The present invention provides compounds, compositions for, and methods of, inhibiting the interactions between MDM2 and p53 for treating cancer. Furthermore the compounds and compositions of the present invention are useful in enhancing the effectiveness of chemotherapy and radiotherapy.

This invention concerns compounds of formula (I)

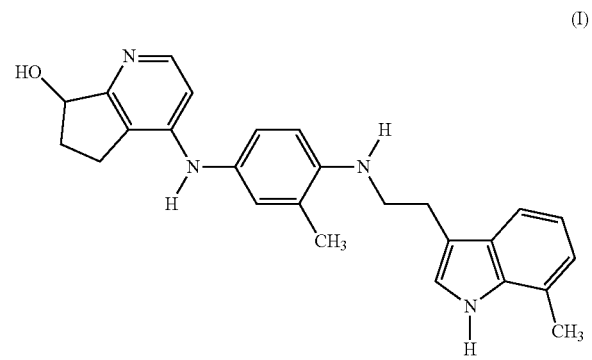 [SMILES: Cc1cc(Nc2ccnc3c2CCC3O)ccc1NCCc1c[nH]c2c(C)cccc12]

a N-oxide form, an addition salt, a stereochemically isomeric form, a solvate thereof, or a polymorphic form thereof.

The compounds of formula (I) may also exist in their tautomeric forms. Such forms although not explicitly indicated in the above formula are intended to be included within the scope of the present invention.

A number of terms used in the foregoing definitions and hereinafter are explained hereunder. These terms are sometimes used as such or in composite terms.

The term "addition salt" comprises the salts which the compounds of formula (I) are able to form with organic or inorganic bases such as amines, alkali metal bases and earth alkaline metal bases, or quaternary ammonium bases, or with organic or inorganic acids, such as mineral acids, sulfonic acids, carboxylic acids or phosphorus containing acids.

The term "addition salt" further comprises pharmaceutically acceptable salts and metal complexes, that the compounds of formula (I) are able to form. Preferably, the term addition salt means the pharmaceutically acceptable salts, in particular the pharmaceutically acceptable acid addition salts.

The term "pharmaceutically acceptable salts" means pharmaceutically acceptable acid or base addition salts. The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) can be converted in their pharmaceutically acceptable acid addition salts by treating the compound with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) can be converted in their pharmaceutically acceptable base addition salts by treating the compound with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term solvate comprises the hydrates and solvent addition forms which the compounds of formula (I) are able to form, as well as the salts thereof. Examples of such forms are e.g. hydrates, alcoholates and the like.

The term "metal complexes" means a complex formed between a compound of formula (I) and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like.

The term "stereochemically isomeric forms of compounds of formula (I)", as used hereinbefore, defines all possible compounds made up of the same atoms bonded by the same sequence of bonds but having different three-dimensional structures which are not interchangeable, which the compounds of formula (I) and their N-oxides, pharmaceutically acceptable salts or physiologically functional derivatives may possess. Unless otherwise mentioned or indicated, the chemical designation of compounds denotes the mixture of all possible stereochemically isomeric forms. In particular, stereogenic centers may have the R- or S-configuration. Hereinafter, particular enantiomers can be indicated as enantiomer A or enantiomer B. Whether the enantiomer is indicated as A or B depends on whether it is isolated first (i.e. A) or second (i.e. B) in the synthesis protocol. Unless otherwise mentioned or indicated, the chemical designation of a compound encompasses the mixture of all possible stereochemically isomeric forms which said compound may possess.

Of special interest are those compounds of formula (I) which are stereochemically pure.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

The N-oxide forms of the compounds of formula (I) are meant to comprise those compounds of formula (I) wherein one or several tertiary nitrogen atoms are oxidized to the so-called N-oxide.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

The present invention is also intended to include any isotopes of atoms present in the compounds of the invention. For example, isotopes of hydrogen include tritium and deuterium and isotopes of carbon include C-13 and C-14.

Whenever used hereinafter, the term "compounds of formula (I)" or "compounds of the present invention" is meant to include also the N-oxide forms, the acid or base addition salts, in particular the acid addition salts, all stereoisomeric forms, the solvates, and all polymorphic crystalline forms or amorphous forms.

Thus, the compounds of the present invention may have one or more polymorph crystalline or amorphous forms and as such are intended to be included in the scope of the invention.

An amorphous form is a form in which a three-dimensional long-range order does not exist. In the amorphous form the position of the molecules relative to one another are essentially random, i.e. without regular arrangement of the molecules on a lattice structure. Amorphous and disordered materials often have improved properties, but generating and stabilising this state can be a big challenge.

A crystal or crystalline form is the form in which the position of the molecules relative to one another is organised according to a three-dimensional lattice structure. Crystalline forms typically include polymorphs and pseudopolymorphs. Polymorphs are different crystalline forms of the same compound resulting from different arrangement of the molecules in the solid state. Different polymorphs have different crystal structures due to a different packing of the molecules in the lattice. This results in a different crystal symmetry and/or unit cell parameters. Polymorphs differ from each other in their physicochemical parameters but not in their chemical composition. Polymorphism is usually difficult to control and poses challenges to the galenists. Pseudopolymorphs, also referred to as solvates, are a particular case of solid state crystalline forms in which either stoichiometric or non-stoichiometric amounts of solvent molecules are present or incorporated into the lattice structure of the compound. A water solvate is also referred to as a hydrate.

Solid state chemistry is of interest to the pharmaceutical industry and especially to those involved in the development of suitable dosage forms. For example, solid state transformations may seriously impact the stability of pharmaceutical drugs (shelf-life). A metastable pharmaceutical solid form can change into a crystalline structure (e.g. from amorphous to crystalline) or solvate/desolvate in response to changes in environmental conditions, processing, or over time.

Different crystal forms or amorphous forms of the same drug may have substantial differences in such pharmaceutically important properties as dissolution rates, thermodynamic solubility and bioavailability. The rate of dissolution of an active ingredient in a patient's stomach fluid may have therapeutic consequences since it imposes an upper limit on the rate at which an orally-administered active ingredient may reach the patient's bloodstream. The rate of dissolution is thus a consideration in formulating solid dosage forms and liquid medicaments such as syrups and elixirs.

Likewise, different crystals or amorphous form may have different processing properties, such as hygroscopicity, flowability, compactation, and the like, which could affect their suitability as active pharmaceuticals for commercial production.

During the clinical development of pharmaceutical drugs, if the polymorphic form is not held constant, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations.

Preferred compounds of formula (I) are compound No. 1 or compound No. 2.

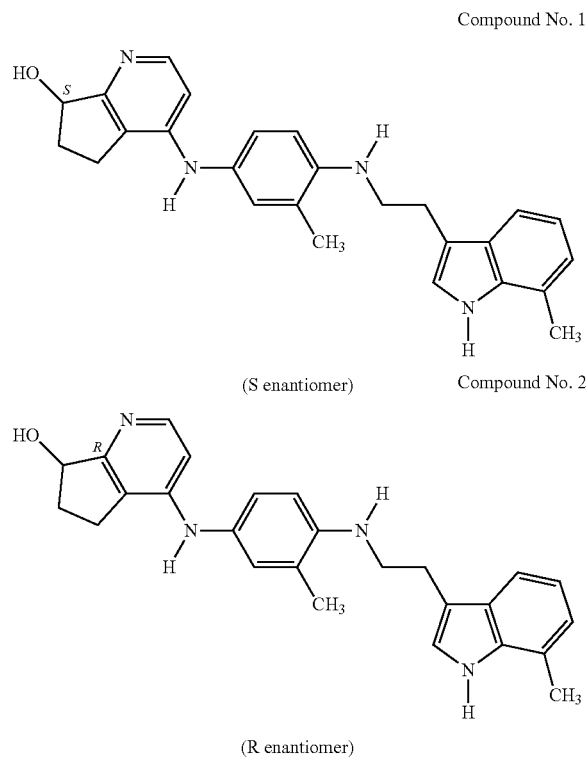

Compound No. 1
(S enantiomer)

Compound No. 2
(R enantiomer)

Other preferred compounds of formula (I) are compound No. 1 or compound No. 3.

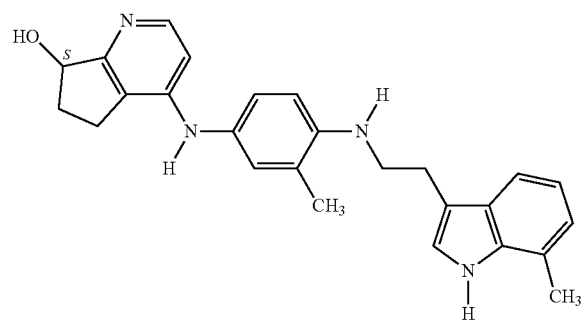

Compound No. 1 (S enantiomer)
Compound No. 3 (S enantiomer, HCl salt)

The preferred compound of formula (I) is compound No. 1.

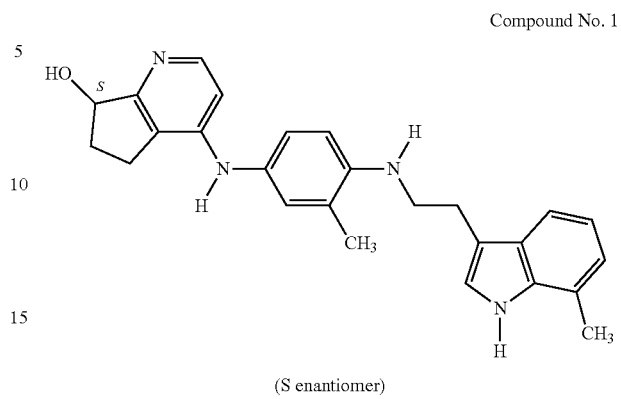

Compound No. 1
(S enantiomer)

or a pharmaceutically acceptable acid addition salt thereof.

The most preferred compound of formula (I) is compound No. 1.

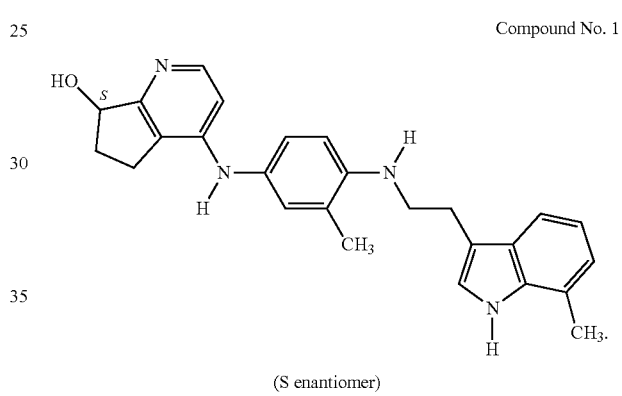

Compound No. 1
(S enantiomer)

Characterization of the Crystalline Forms

In one embodiment, the present invention provides compounds of formula (I) in solid state further characterized in that they are in crystalline form.

In another embodiment, the invention provides the crystalline forms of the compound No. 1 selected from Form I and Form II. These forms are substantially free from impurities. Suitably, these forms contain no more than 10% of impurities, more suitably they contain no more than 5% of impurities, even more suitably they contain no more than 1% of impurities. Polymorphic purity may be tested by XRPD, with the area under the peaks used to calculate polymorphic purity. These forms are preferably essentially pure. With the term "essentially pure" is meant more than 90% pure, suitably more than 95% pure, more suitably more than 97% pure, most suitably more than 99% pure.

The present invention further provides a mixture of two or more crystalline forms of compound No. 1, wherein at least one crystalline form is selected from Form I or Form II.

The present invention further provides a mixture of one or more crystalline forms of a compound of formula (I), preferably compound No. 1, and an amorphous form of the compound of formula (I).

The characterising XRPD intensity peak positions of Form I and Form II are given in degrees two-theta.

Form I of compound No. 1 is characterized by typical diffraction peaks at two-theta positions 6.4°±0.2°, 12.8°±0.2°, 15.2°±0.2° and 17.3°±0.2°.

Form II of compound No. 1 is characterized by typical diffraction peaks at two-theta positions 8.0°±0.2°, 12.5°±0.2°, 18.2°±0.2°, 21.9°±0.2° and 27.5°±0.2°.

The X-ray powder diffraction pattern (XRPD) of Form I is as substantially depicted in FIG. 2. The X-ray powder diffraction pattern of Form II is as substantially depicted in FIG. 5.

The XRPD data and pattern representations of all forms were obtained using a Philips X'PertPRO MPD diffractometer PW3050/60 with a generator PW3040. The instrument was equipped with a Cu LFF X-ray tube PW3373/10. The compound to be analysed was spread on a zero background sample holder. The instruments parameters were as follows:
  generator voltage: 45 kV
  generator amperage: 40 mA
  geometry: Bragg-Brentano
  stage: spinner stage.

The scanning parameters for Forms I and II were as follows: the range was 3° to 50° 2-theta with a continuous scan at a rate of 0.0167°/step, at 30 sec/step. The spinner revolution time was 1 sec, the radiation type CuKα, and the radiation wavelength was 1.5406 Å.

The Incident beam path parameters for Forms I and II were as follows:
  program divergence slit: 15 mm
  Soller slit: 0.04 rad
  beammask: 15 mm
  antiscatter slit: 1°
  beamknife: +

The diffracted beam path parameters for Forms I and II were as follows:
  long anti scatter shield: +
  Soller slit: 0.04 rad
  Ni filter: +
  detector: X'Celerator The accuracy of the XRPD peak positions provided for Forms I and II is defined as 0.2° due to experimental differences, such as instrumentations, sample preparations, and the like.

The characterising IR absorbance peak positions of Forms I and II are given in wavenumbers $cm^{-1}$.

Form I of compound No. 1 is characterized by an infrared spectrometry (IR) micro attenuated reflectance spectrum with typical absorption bands at 3403±1 $cm^{-1}$, 3150±1 $cm^{-1}$, 1595±1 $cm^{-1}$, 1517±1 $cm^{-1}$, 1320±1 $cm^{-1}$, 1165±1 $cm^{-1}$, 1071±1 $cm^{-1}$, 882±1 $cm^{-1}$, 819±1 $cm^{-1}$, 781±1 $cm^{-1}$ and 733±1 $cm^{-1}$.

Form II of compound No. 1 is characterized by an infrared spectrometry micro attenuated reflectance spectrum with typical absorption bands at 3411±1 $cm^{-1}$, 3352±1 $cm^{-1}$, 1600, 1508, 1480, 1327, 1171, 1079, 810, 770 and 743 $cm^{-1}$±1 $cm^{-1}$.

The IR spectrum of Form I is as substantially depicted in FIG. 1. The IR spectrum of Form II is as substantially depicted in FIG. 4.

The IR data and spectrum representations were obtained using infrared spectrometry micro Attenuated Total Reflectance (microATR) with a spectrometer. The microATR accessory was a Harrick Split Pea with Si crystal. The detector used was a DTGS with KBr windows. The scan parameters for Forms I and II were as follows:
  number of scans: 32
  resolution: 1 $cm^{-1}$
  wavelength range: 4000 to 400 $cm^{-1}$
  baseline correction: yes
  beamsplitter: Ge on KBr.

The accuracy of the IR absorbance peaks provided for Forms I and II is defined as 1 $cm^{-1}$ due to experimental differences, such as instrumentations, sample preparations, and the like.

The characterising differential scanning calorimetry (DSC) endothermic peak positions or ranges of Forms I and II are given in ° C.

Form I of compound No. 1 melts at about 191.9° C. The heat of fusion is 113 J/g.

Form II of compound No. 1 melts at about 185.6° C., the heat of fusion is 82 J/g. An extra endothermic signal in the DSC curve is observed at about 158.5° C. (2 J/g) probable due to an impurity present in the sample.

The DSC curve of Form I is as substantially depicted in FIG. 3. The DSC curve of Form II is as substantially depicted in FIG. 6.

The DSC data and curve representations were obtained using a TA-Instruments Q1000 MTDSC equipped with a RCS cooling unit. The weight of the samples was about 3 mg, which were transferred into a standard aluminum TA-Instrument sample pan. The samples were scanned at a rate of 10° C./min from 25° C. to a final temperature of 300° C. The oven was constantly purged with nitrogen gas at a flow rate of 50 ml/min.

The tolerance of the DSC curves provided for Forms I and II is defined as 3° C. due to experimental differences, such as instrumentations, sample preparations, and the like.

The compounds of formula (I), their pharmaceutically acceptable salts and N-oxides and stereochemically isomeric forms thereof may be prepared in conventional manner. The starting materials and some of the intermediates are known compounds and are commercially available or may be prepared according to conventional reaction procedures as generally known in the art, more specifically as disclosed in EP 1809622.

A number of such preparation methods will be described hereinafter in more detail. Analogues methods for obtaining compounds of formula (I) are described in the examples.

The compounds of formula (I) can be prepared by reacting an intermediate of formula (II) with an intermediate of formula (III) wherein W is an appropriate leaving group such as, for example, halo, e.g. fluoro, chloro, bromo or iodo, or a sulfonyloxy radical such as methylsulfonyloxy, 4-methylphenylsulfonyloxy and the like. The reaction can be performed in a reaction-inert solvent such as, for example, an alcohol, e.g. methanol, ethanol, 2-methoxy-ethanol, propanol, butanol and the like; an ether, e.g. 1,4-dioxane, 1,1'-oxybispropane and the like; a ketone, e.g. 4-methyl-2-pentanone; or N,N-dimethylformamide, nitrobenzene, acetonitrile, acetic acid and the like. The addition of an appropriate base such as, for example, an alkali or earth alkaline metal carbonate or hydrogen carbonate, e.g. triethylamine or sodium carbonate, may be utilized to pick up the acid which is liberated during the course of the reaction. A small amount of an appropriate metal iodide, e.g., sodium or potassium iodide may be added to promote the reaction. Stirring may enhance the rate of the reaction. The reaction may conveniently be carried out at a temperature ranging between room temperature and the reflux temperature of the reaction mixture and, if desired, the reaction may be carried out at an increased pressure.

Alternatively the compounds of formula (I) can be prepared by reacting the aniline of formula (II) with the intermediate of formula (III) in the presence of an appropriate catalyst such as, for example, tris[μ-[(1,2-η:4,5-η)-(1E,4E)-1,5-diphenyl-1,4-pentadien-3-one]]dipalladium ($Pd_2(dba)_3$) and an appropriate ligand such as, for example (9,9-dimethyl-9H-xanthene-4,5-diyl)bis[diphenylphosphine] (Xantphos). The reaction can be performed in a reaction inert solvent such as, for example dioxane and appropriate bases such as, for example, sodium tert-butoxide and $K_3PO_4$ can be added.

$C_{1-6}$alkyloxy, e.g. methyloxy, in diisopropylethyl amine $C_{1-6}$alkyl represents a straight or branched saturated hydrocarbon radical having from 1 to 6 carbon atoms such as for example methyl, ethyl, propyl, 2-methyl-ethyl, pentyl, hexyl and the like.

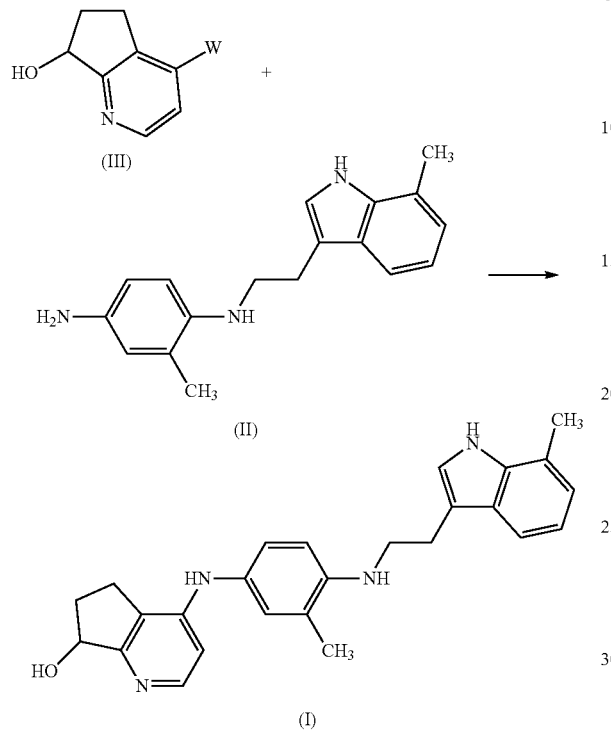

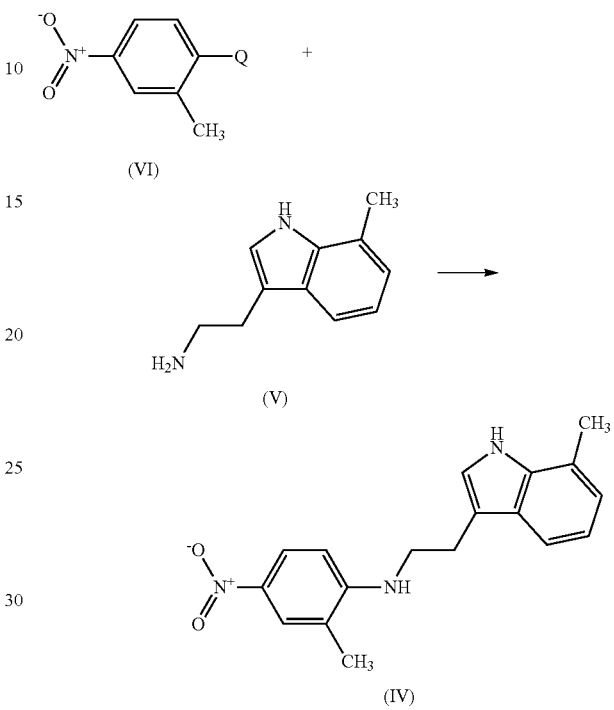

The intermediates of formula (II) can be prepared by hydrogenating an intermediate of formula (IV) in the presence of palladium on carbon, platinum on carbon or Raney nickel under pressure and in a suitable solvent such as toluene, with the formation of the intermediate of formula (II).

The intermediates of formula (III) can be prepared by stirring the intermediate of formula (VII) in a mixture of methanol/$NH_3$. If desired the intermediate of formula (III) can be converted to the intermediate of formula (VII) by stirring in a mixture of acetic anhydride and pyridine.

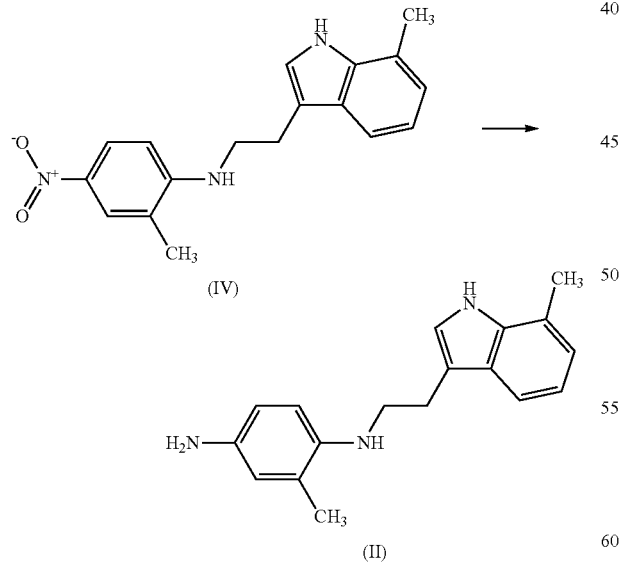

The intermediates of formula (IV) can be prepared by reacting an intermediate of formula (V) with an intermediate of formula (VI), wherein Q is an appropriate leaving group such as, for example, halo, e.g. fluoro, chloro, bromo or iodo, or The S-enantiomer of intermediate (III), herein referred to as the intermediate of formula (III-a), and the R-enantiomer of the intermediate of formula (VII), herein referred to as the intermediate of formula (VII-b), can be prepared by adding Lipase Candida Antartica B to a racemic mixture of the intermediate of formula (III) in a suitable solvent such as acetic acid ethenyl ester (see Scheme 1). When desired the intermediate of formula (VII-b) can be converted into the R enantiomer of intermediate (III), herein referred to as intermediate of formula (III-b), by reaction in MeOH/$NH_3$.

Starting from the racemic mixture this method affords the conversion of one of the enantiomers in it's acetate with ee>99% and 58% yield and the second enantiomer is isolated with ee>99% in 42% yield.

Scheme 1

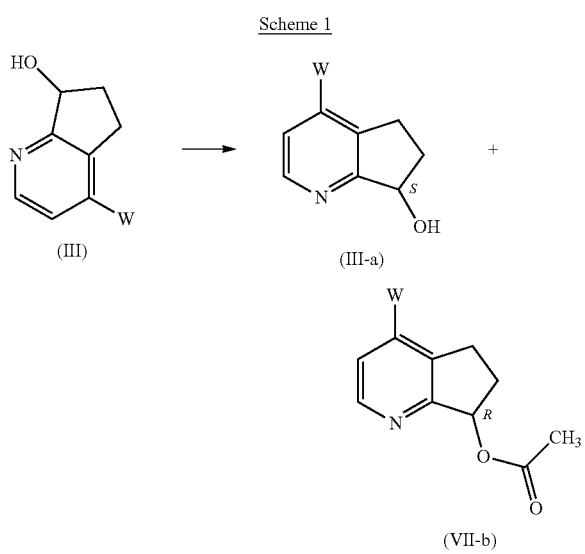

Alternatively, the R-enantiomer of intermediate (III), herein referred to as the intermediate of formula (III-b), and the S-enantiomer of the intermediate of formula (VII), herein referred to as the intermediate of formula (VII-a), can be prepared by adding Lipase *Candida Antartica* B to a racemic mixture of the intermediate of formula (VII) in water (see Scheme 2). When desired intermediate (VII-a) can be converted into intermediate (III-a) by reaction in MeOH/NH$_3$.

Scheme 2

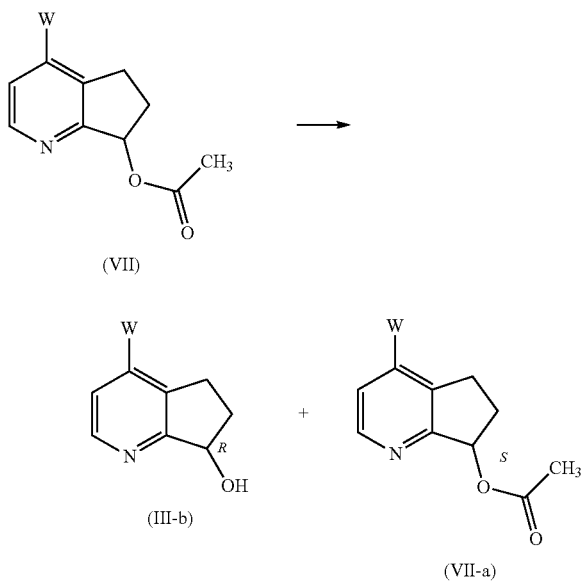

Alternatively, the intermediate of formula (III) can also be separated into its enantiomers by chiral column chromatography.

The intermediates of formula (VII) can be prepared by stirring the intermediate of formula (VIII) in acetic anhydride.

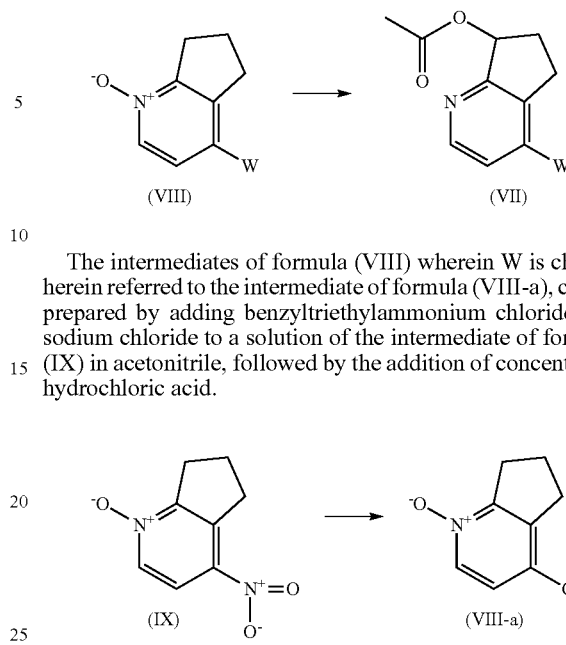

The intermediates of formula (VIII) wherein W is chloro, herein referred to the intermediate of formula (VIII-a), can be prepared by adding benzyltriethylammonium chloride and sodium chloride to a solution of the intermediate of formula (IX) in acetonitrile, followed by the addition of concentrated hydrochloric acid.

The intermediates of formula (IX) can be prepared by adding fuming nitric acid to sulfuric acid followed by portionwise addition of 6,7-dihydro-5H-cyclopenta[b]pyridine, 1-oxide.

The compounds of formula (I) and some of the intermediates in the present invention contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization, supercritical fluid chromatography or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

The compounds of formula (I), the pharmaceutically acceptable acid addition salts, the stereoisomeric forms and the polymorphic forms thereof have valuable pharmacological properties in that they inhibit the interaction between p53 and MDM2.

The term "MDM2" (Murine Double Minute2) is used herein to mean a protein obtained as a result of expression of the mdm2 gene. Within the meaning of this term, MDM2 encompass all proteins encoded by mdm2, mutants thereof, alternative slice proteins thereof, and phosphorylated proteins thereof. Additionally, as used herein, the term "MDM2" includes MDM2 analogues, e.g. MDMX, also known as MDM4, and MDM2 homologues and analogues of other animals, e.g. the human homologue HDM2 or the human analogue HDMX.

The term "inhibiting the interaction" or "inhibitor of the interaction" is used herein to mean preventing or reducing the direct or indirect association of one or more molecules, peptides, proteins, enzymes or receptors; or preventing or reducing the normal activity of one or more molecules, peptides, proteins, enzymes, or receptors.

The term "inhibitor of the interaction of p53 with MDM2" or "p53-MDM2 inhibitor" is used herein to describe an agent which increases the expression of p53 in the assay described in C.1. This increase may be caused by, but is not limited to, one or more of the following mechanisms of action:

- inhibiting the interaction between p53 and MDM2,
- direct association with either the MDM2 or the p53 protein,
- interactions with upstream or downstream targets, e.g. kinases, or enzyme activities involved in ubiquitination or SUMO modification,
- sequestering or transportation of MDM2 and p53 into different cellular compartments,
- modulation of proteins associating with MDM2, for example (but not limited to), p63, p73, E2F-1, Rb, p21waf1 or cip1, HIF1alpha, Foxo3A, p14ARF,
- downregulating or interference with MDM2 expression and/or MDM2 activity, for example (but not limited to), impacting on its cellular localisation, post-translational modification, nuclear export, ubiquitin ligase activity or interference with binding of MDM2 with the proteasome, modulating the MDM2-proteasome interaction,
- direct or indirect stabilization of the p53 protein, e.g. by keeping it in its functional structural form, or by preventing misfolding,
- enhancing p53 expression or expression of p53 family members, e.g. p63 and p73.
- increasing p53 activity, for example by (but not limited to), enhancing its transcriptional activity and/or
- increasing expression of genes and proteins of the p53-signalling pathway, for example (but not limited to) p21waf1, cip1, MIC-1 (GDF-15), PIG-3, Bax, Puma, Noxa, and ATF-3.

Hence, the present invention discloses the compounds of formula (I) for use as a medicine, in particular for the treatment of cancer or related diseases, for inhibiting tumour growth, for inhibiting the interaction between MDM2 and p53, for modulating the MDM2-proteasome interaction.

Furthermore, the invention also concerns the use of a compound for the manufacture of a medicament for the treatment of a disorder mediated through a p53-MDM2 interaction, wherein said compound is a compound of formula (I)

The term "treating" or "treatment" as used herein covers any treatment of a disease and/or condition in an animal, particularly a human, and includes: (i) preventing a disease and/or condition from occurring in a subject which may be predisposed to the disease and/or condition but has not yet been diagnosed as having it; (ii) inhibiting the disease and/or condition, i.e., arresting its development; (iii) relieving the disease and/or condition, i.e., causing regression of the disease and/or condition.

With the term "a disorder mediated through a p53-MDM2 interaction" is meant any undesired or detrimental condition that results from the interaction between the MDM2 protein and p53 or other cellular proteins that induce apoptosis, induce cellular death, or regulate the cell cycle.

This invention also provides a method for treating a disorder mediated through a p53-MDM2 interaction by administering an effective amount of a compound of the present invention, to a subject, e.g. a mammal (and more particularly a human) in need of such treatment.

The compounds of the invention can have antiproliferative effects in tumour cells, even if such cells are devoid of functional p53. More in particular, the compounds of the invention can have antiproliferative effects in tumours with wild-type or mutant p53 and/or in tumours overexpressing MDM2.

Thus, this invention also provides a method for inhibiting tumour growth by administering an effective amount of a compound of the present invention, to a subject, e.g. a mammal (and more particularly a human) in need of such treatment.

Examples of tumours including adult and pediatric malignancies, which may be inhibited by the compounds of the present invention include, but are not limited to, lung cancer including small cell lung cancer and non-small cell lung cancer (e.g. adenocarcinoma), pancreatic cancers, colon cancers (e.g. colorectal carcinomas, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemias (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcomas, liposarcomas, gastrointestinal stromal sarcomas, malignant peripheral nerve sheath tumours (MPNST), Ewing sarcomas, leiomyosarcomas, mesenchymal chondrosarcomas, lymphosarcomas, fibrosarcomas, rhabdomyosarcomas, melanomas, teratocarcinomas, neuroblastomas, brain tumours, gliomas, benign tumour of the skin (e.g. keratoacanthomas), breast carcinoma (e.g. advanced breast cancer), kidney carcinoma, ovary carcinoma, cervical carcinoma, endometrial carcinoma, bladder carcinoma, prostate cancer including the advanced disease and hormone refractory prostate cancer, testicular cancers, osteosarcoma, head and neck cancer, epidermal carcinoma, multiple myeloma (e.g. refractory multiple myeloma), mesothelioma. Particular cancers that can be treated with the compounds of the present invention are breast cancer, colorectal cancer, non-small cell lung cancer, acute myelogenous leukemia (AML).

The compounds of the present invention can also be used for the treatment and prevention of inflammatory conditions.

Thus, this invention also provides a method for the treatment and prevention of inflammatory conditions by administering an effective amount of a compound of the present invention, to a subject, e.g. a mammal (and more particularly a human) in need of such treatment.

The compounds of the present invention can also be used for the treatment of autoimmune diseases and conditions. With the term "autoimmune diseases" is meant any disease in which an animal's immune system reacts adversely to a self-antigen. With the term "self-antigen" is meant any antigen that is normally found in the animal's body. Representative autoimmune diseases include but are not limited to: Hashimoto's thyroiditis, Grave's disease, multiple sclerosis, pernicious anemia, Addison's disease, insulin-dependent diabetes mellitus, rheumatoid arthritis, systemic lupus erythematosus (SLE or lupus), dermatomyositis, Crohn's disease, Wegener's granulomatosis, Anti Glomerular Basement Membrane Disease, Antiphospholipid Syndrome, 25 Dermatitis Herpetiformis, Allergic Encephalomyelitis, Glomerulonephritis, Membranous Glomerulonephritis, Goodpasture Syndrome, Lambert-Eaton, Myasthenic Syndrome, Myasthenia Gravis, Bullous Pemphigoid, Polyendocrinopathies, Reiter's Disease, and Stiff-Man Syndrome.

Thus, this invention also provides a method for the treatment of autoimmune diseases and conditions by administering an effective amount of a compound of the present invention, to a subject, e.g. a mammal (and more particularly a human) in need of such treatment.

The compounds of the present invention can also be useful for the treatment of diseases associated with conformational unstable or misfolded proteins.

Examples of diseases associated with conformational unstable or misfolded proteins include but are not limited to: cystic fibrosis (CFTR), Marfan syndrom (fibrillin), Amyotrophic lateral sclerosis (superoxide dismutase), scurvy (collagen), maple syrup urine disease (alpha-ketoacid dehydrogenase complex), osteogenesis imperfecta (type1 procollagen pro-alpha), Creutzfeldt-Jakob disease (prion), Alzheimer's disease (beta-amyloid), familial amyloidosis (lysozyme), cataracts (crystallins), familial hypercholesterolemia (LDL receptor), $\alpha$1-antitrypsin deficiency, Tay-Sachs disease (beta-hexosaminidase), retinitis pigmentosa (rhodopsin), and leprechaunism (insulin receptor).

Thus, this invention also provides a method for the treatment of diseases associated with conformational unstable or misfolded proteins by administering an effective amount of a compound of the present invention, to a subject, e.g. a mammal (and more particularly a human) in need of such treatment.

In view of their useful pharmacological properties, the subject compounds may be formulated into various pharmaceutical forms for administration purposes.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to inhibit the interaction between MDM2 and p53 or other cellular proteins that induce apoptosis, induce cellular death, or regulate the cell cycle, in particular an amount sufficient to modulate the MDM2-proteasome interaction.

The oncogenic potential of MDM2 is not only determined by its ability to suppress p53, but also by its ability to regulate other tumour suppressor proteins, e.g. the retinoblastoma protein pRb and the closely associated E2F1 transcription factor, p63, p73.

Thus, the compound of the invention is administered in an amount sufficient to modulate the interaction between MDM2 and the E2F1 transcription factors.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a p53-MDM2 inhibitor with another anticancer agent is envisaged, especially for use as a medicine, more specifically in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoïden for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, caminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat or metastat.
- Recombinant interleukins for example aldesleukin, denileukin diftitox, interferon alfa 2a, interferon alfa 2b, peginterferon alfa 2b
- MAPK inhibitors
- Retinoids for example alitretinoin, bexarotene, tretinoin
- Arsenic trioxide
- Asparaginase
- Steroids for example dromostanolone propionate, megestrol acetate, nandrolone (decanoate, phenpropionate), dexamethasone
- Gonadotropin releasing hormone agonists or antagonists for example abarelix, goserelin acetate, histrelin acetate, leuprolide acetate
- Thalidomide, lenalidomide
- Mercaptopurine, mitotane, pamidronate, pegademase, pegaspargase, rasburicase
- BH3 mimetics for example ABT-737
- MEK inhibitors for example PD98059, AZD6244, CI-1040
- colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

As stated above, the compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays.

Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the p53-MDM2 inhibitor according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the p53-MDM2 inhibitor according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a p53-MDM2 inhibitor according to the invention and as further active ingredient one or more anticancer agent, as a combined preparation for simultaneous, separate or sequential use in the treatment of patients suffering from cancer.

The one or more other medicinal agents and p53-MDM2 inhibitor may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and p53-MDM2 inhibitor being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

These dosages may be administered for example once, twice or more per course of treatment, which may be repeated for example every 7, 14, 21 or 28 days.

The compounds of formula (I), the pharmaceutically acceptable acid addition salts and stereoisomeric forms thereof can have valuable diagnostic properties in that they can be used for detecting or identifying a p53-MDM2 interaction in a biological sample comprising detecting or measuring the formation of a complex between a labelled compound and/or p53 and/or MDM2 and or other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^3$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase. Biological samples can be defined as body tissue or body fluids. Examples of body fluids are cerebrospinal fluid, blood, plasma, serum, urine, sputum, saliva and the like.

The following examples illustrate the present invention.

EXPERIMENTAL PART

Hereinafter, "DMF" is defined as N,N-dimethylformamide, "DCM" is defined as dichloromethane, "EtOAc" is defined as ethyl acetate, "EtOH" is defined as ethanol, "MeOH" is defined as methanol, "DIPEA" is defined as N-ethyl-N-(1-methylethyl)-2-propanamine, "Et₃N" is defined as triethylamine and "DMAP" is defined as 4-(dimethylamino)pyridine.

A. Preparation of the Intermediate Compounds

Example A1 a) Preparation of Intermediate 1

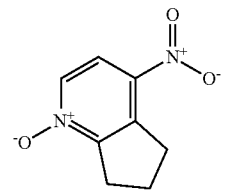

Fuming nitric acid (50 ml) was added slowly to sulfuric acid (50 ml) at room temperature. Then, the mixture was stirred at 50° C. 6,7-dihydro-5H-cyclopenta[b]pyridine, 1-oxide (0.146 mol) was added portionwise. The mixture was stirred at 70° C. for 15 minutes and was then poured out into a H₂O/ice mixture. The product was extracted with DCM. The separated organic layer was washed 3 times with H₂O (200 ml), dried (MgSO₄), filtered and the solvent was evaporated. The residue was purified by column chromatography over silica gel (eluent: DCM/MeOH 98/2; 20-45 μm). The pure fractions were collected and the solvent was evaporated. Yield: 12 g of intermediate 1 (45%).

b) Preparation of Intermediate 2

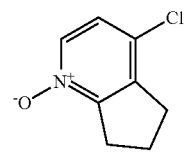

Benzyltriethylammonium chloride (0.013 mol) and NaCl (0.266 mol) were added to a solution of intermediate 1 (0.067 mol) in CH₃CN (23 ml). Then concentrated HCl (23 ml) was added and the mixture was stirred and refluxed for 18 hours. H₂O was added. The solution was filtered over Celite. The filtrate was extracted 4 times with DCM. The separated organic layer was dried (MgSO₄), filtered and the solvent was evaporated. The residue was purified by column chromatography over silica gel (eluent: DCM/MeOH/NH₄OH 98/2/0 to 95/5/0.1; 20-45 μm). The desired fraction was collected and the solvent was evaporated. Yield: 11 g of intermediate 2.

c) Preparation of Intermediate 3

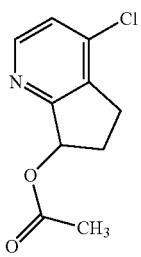

A mixture of intermediate 2 (0.065 mol) in acetic anhydride (110 ml) was stirred for 30 minutes at 100° C. Then the mixture was concentrated and the crude oil was dissolved in DCM. The organic layer was washed with $K_2CO_3$ (10%), dried ($MgSO_4$), filtered and the solvent was evaporated. Yield: 12.5 g of intermediate 3.

Intermediate 3 can also be prepared as follows:

a-1) Preparation of Intermediate a

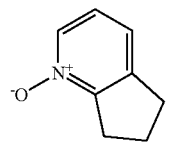

174 g 3-chloroperoxybenzoic acid (mCPBA) (1.6 eq) was added to 1 L ethyl acetate (EtOAc) (6 mL/g mCPBA). The reaction mixture (mixture A) was stirred for 10 minutes at ambient temperature. 76 g

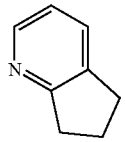

(0.641 mol) was dissolved in 375 ml EtOAc (5 mL/g). This solution was added dropwise to reaction mixture A over 20 minutes keeping the temperature constant at 10° C. The mixture was stirred overnight at ambient temperature. The reaction mixture was washed two times with a solution of 27 g $NaHSO_3$ (0.25 mols/mol mCPBA) in 300 mL $H_2O$ (11 mL/g $NaHSO_3$) and the water layers were combined. The organic layer (+intermediate layer) was extracted with 300 mL $H_2O$ (4 mL/g). The two layers were separated. The 2 water layers were joined (pH: +/−5) and neutralized with $Na_2CO_3$ until pH: 8. The product was extracted from the water layer by continuous extraction with dichloromethane for one night. The two layers were separated. The organic layer was dried with $MgSO_4$. The $MgSO_4$ was filtered off and the filtrate was concentrated under reduced pressure. Yield: 49.5 g (57%) of intermediate a (off-white product)

b-1) Preparation of Intermediate b

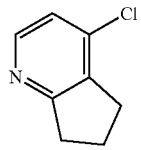

A solution of 49.5 g intermediate a (0.366 mol), 15.5 g lithiumchloride (LiCl) (1 eq) and 495 mL acetonitrile (10 mL/g) was prepared and stirred for 10 minutes at ambient temperature. 102 mL phosphoroxychloride ($POCl_3$) (3 eq) was added dropwise to the reaction mixture. The reaction mixture was heated to 80° C. and stirred for one night. The reaction mixture was cooled to 45° C. and 750 mL $H_2O$ (15 mL/g) was added dropwise, while keeping the temperature between 40° C. and 50° C., over 1 hour. The reaction mixture was cooled to ambient temperature and stirred for 2 hours at ambient temperature. 213 g $Na_2CO_3$ (5.5 eq) was added and stirred for 30 minutes at ambient temperature. Further $Na_2CO_3$ was added and stirring for 10 minutes at ambient temperature. 750 mL diisopropylether (DIPE) (15 mL/g) was added and 500 mL $H_2O$ (10 mL/g). The mixture was stirred for 10 minutes at ambient temperature. The reaction mixture was filtered over dicalite. The layers were separated. The organic layer was dried with $MgSO_4$. $MgSO_4$ was filtered off. The filtrate was concentrated under reduced pressure. Yield: 51 g (91%) (brown oil) of intermediate b.

c-1) Preparation of Intermediate c

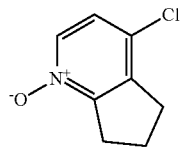

108 g mCPBA (1.2 eq) was added to 750 mL DCM (7 mL/g mCPBA). The mixture was stirred at ambient temperature for 10 minutes. 60 g of intermediate b (0.391 mol) was dissolved in 600 mL DCM (10 mL/g). This solution was added dropwise to the mCPBA reaction mixture over 20 minutes keeping the temperature constant at 10° C. The mixture was stirred overnight at ambient temperature. To the reaction mixture was added a solution of 33 g $NaHSO_3$ (0.5 mols/mol mCPBA) in 330 mL $H_2O$ (10 mL/g $NaHSO_3$). The reaction mixture was stirred vigorously for 30 minutes at ambient temperature. 1 L $H_2O$ (17 mL/g) was added. 203 g $Na_2CO_3$ (5 eq) was added. 1 L $H_2O$ (17 mL/g) was added. The mixture was stirred at ambient temperature for 30 minutes. The two layers were separated. The water layer was extracted three times with 500 mL DCM. The organic layers were combined and stirred for 30 minutes at ambient temperature. The organic layer was dried with $MgSO_4$. The $MgSO_4$ was filtered off. The filtrate was reduced to 500 mL. A solution of 65 g $NaHSO_3$ (1 moles/mole mCPBA) in 260 mL $H_2O$ (4 mL/g $NaHSO_3$) was added. The reaction mixture was stirred vigorously for 2 hours. The two layers were separated. The water layer was extracted two times with 200 mL DCM. The 3 organic layers were combined and dried with MgSO$_4$. The MgSO$_4$ was filtered off. The filtrate was concentrated under reduced pressure. Yield: 56.3 g (85%) (grey product) of intermediate c.

d-1) Preparation of Intermediate 3

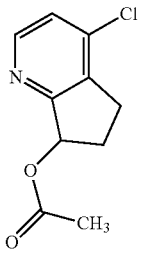

56 g of intermediate c (0.330 mol) was added to 170 mL acetic anhydride (Ac$_2$O) (3 mL/g). The mixture was stirred at ambient temperature during 10 minutes The reaction mixture was heated to 100° C. and kept at 100° C. and stirred at 100° C. for 2 hours. The reaction mixture was cooled to ambient temperature. The reaction mixture was added dropwise over 20 minutes to 560 mL H$_2$O (10 mL/g and stirred at ambient temperature for 1 hour. 90 g K$_2$CO$_3$ (2 eq) was added. The reaction mixture was filtered over dicalite. 800 mL DCM (14 mL/g) was added to the reaction mixture. The reaction mixture was stirred for 30 minutes at ambient temperature. The two layers were separated. The organic layer was dried with MgSO$_4$. The MgSO$_4$ was filtered off. The filtrate was concentrated under reduced pressure. Yield: 21.6 g (31%) (dark-brown oil) of intermediate 3.

d) Preparation of Intermediate 4

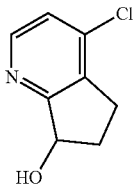

A mixture of intermediate 3 (0.04 mol) in CH$_3$OH/NH$_3$ (90 ml) was stirred at room temperature for 48 hours. Then the mixture was concentrated. The crude oil was dissolved in DCM and K$_2$CO$_3$ was added. The solution was filtered over Celite. The filtrate was extracted with DCM. The separated organic layer was dried (MgSO$_4$), filtered and the solvent was evaporated. Yield: 6.7 g of intermediate 4.

e) Preparation of Intermediate 7 and Intermediate 8

Intermediate 7

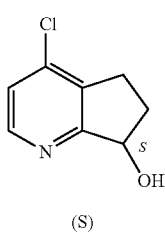
(S)

Intermediate 8

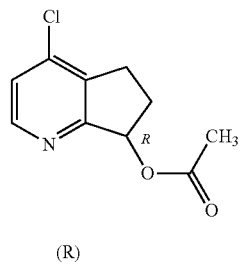
(R)

A mixture of intermediate 4 (5 g, 0.029 mol) and Lipase Candida Antartica B (2.5 g) in acetic acid ethenyl ester (50 ml) was stirred at room temperature for 4 hours. The reaction mixture was filtered over Celite. The Celite was washed with DCM. The filtrate's solvent was evaporated. The residue (6.3 g) was purified by column chromatography over silica gel (eluent: DCM/MeOH from 100/0 till 98/2; 15-40 μm). Two different product fractions were collected and the solvent of each product fraction was evaporated. Yield: 2.1 g of intermediate 7 (42%; S-enantiomer), and 3.6 g of intermediate 8 (58%; R-enantiomer). When desired intermediate 8 can be converted into the R enantiomer of intermediate 7 by reaction in MeOH/NH$_3$.

Example A2 a) Preparation of Intermediate 5

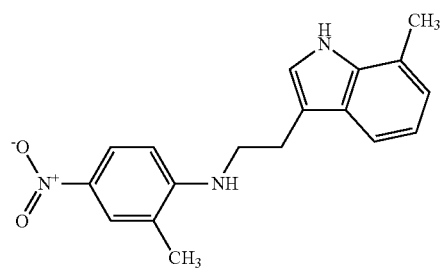

A mixture of 1-fluoro-2-methyl-4-nitro-benzene (0.0103 mol), 7-methyl-1H-indole-3-ethanamine (0.0103 mol) and DIPEA (9 ml, 0.0515 mol) was stirred at 120° C. for 18 hours. Then the mixture was cooled to room temperature, diluted with a small amount of DCM/MeOH and washed with K$_2$CO$_3$ (10%). The organic layer was separated, dried (MgSO$_4$), filtered and the solvent was evaporated till dryness. The residue (4.1 g) was purified by column chromatography over silica gel (eluent: DCM/cyclohexane 70/30; 15-35 μm). The pure fractions were collected and the solvent was evaporated. Yield: 1.45 g of intermediate 5 (45%).

b) Preparation of Intermediate 6

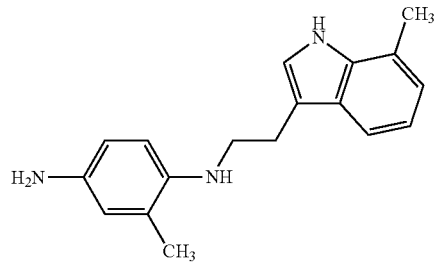 [SMILES: Cc1cc(N)ccc1NCCc1c[nH]c2c(C)cccc12]

A mixture of intermediate 5 (0.0045 mol) and Pt/C 5% (0.15 g) in toluene (40 ml) was hydrogenated at room temperature for 18 hours under a 3 bar pressure. Then the reaction mixture was filtered. The filtrate was evaporated till dryness. Yield: 1.25 g of intermediate 6 (100%).

B. Preparation of the Final Compounds

Example B1

Preparation of Compounds 1 and 2

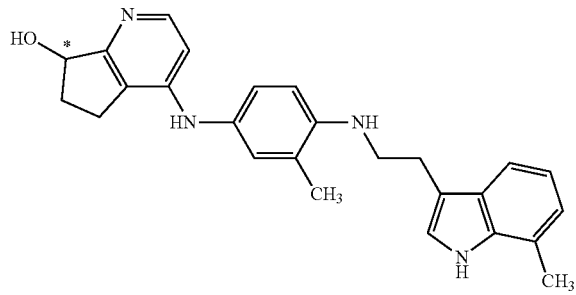

Compound 1 (enantiomer A; S) (chiral center indicated by *)
Compound 2 (enantiomer B; R)

A mixture of intermediate 6 (0.0039 mol), intermediate 4 (0.0042 mol) and HCl/2-propanol (3 drops) in CH$_3$CN (20 ml) was stirred overnight at 65° C. Then K$_2$CO$_3$ (10%) was added. The mixture was extracted with EtOAc. The organic layer was separated, dried (MgSO$_4$), filtered and the solvent was evaporated. The residue (1.8 g) was purified by column chromatography over silica gel (eluent: CH$_2$Cl$_2$/CH$_3$OH/ NH$_4$OH 92/8/0.5; 15-40 µm). The pure fractions were collected and the solvent was evaporated. The residue (0.55 g) was purified by column chromatography over Chiralpack AD (eluent: EtOH/MeOH/2-propanol 50/50/0.3). Two fractions were collected and the solvent was evaporated, yielding 0.24 g of fraction 1 and 0.26 g of fraction 2. Fraction 1 was crystallized from diethyl ether. The precipitate was filtered off and dried. Yield: 0.17 g of compound 1 (enantiomer A; S enantiomer) (11%). Fraction 2 was crystallized from diethyl ether. The precipitate was filtered off and dried. Yield: 0.12 g of compound 2 (enantiomer B; R enantiomer) (8%).

Example B2

Preparation of Compounds 1 and 3

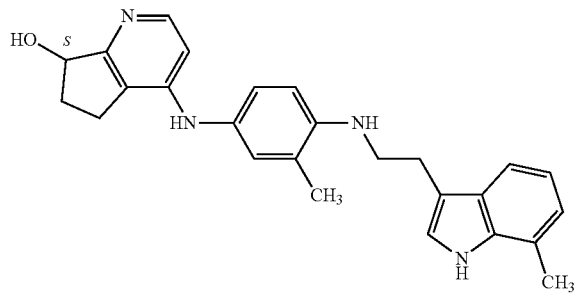

Compound 1 (S-enantiomer)
Compound 3 (S-enantiomer; HCl-salt)

Compound 1 can also be obtained following the procedure described in example B2. A solution of intermediate 6 (11.3 g, 0.04 mol), intermediate 7 (7.5 g, 0.044 mol) and HCl (4 M in dioxane) in CH$_3$CN/EtOH (150 ml) was stirred during the weekend at 65° C. Then K$_2$CO$_3$ (10%) and EtOAc were added and the resulting mixture was extracted with EtOAc. The separated organic layer was dried (MgSO$_4$), filtered and the solvent was evaporated. The residue (23 g) was purified by column chromatography (eluent: DCM/MeOH/NH$_4$OH 92/7/1). The pure fractions were collected and the solvent was evaporated. The residue (14.2 g, 85%) was crystallized from CH$_3$CN. The precipitate was filtered off and dried. Yield: 10.4 g of compound 1 (63%). Part of this product (1.3 g) was dissolved in MeOH. HCl in 2-propanol (5 N; 2 equivalents, 2.6 ml) was added dropwise at 5° C. The mixture was stirred at 5° C. overnight. Then CH$_3$CN was added and the product was crystallized from this mixture (MeOH/CH$_3$CN) (the solution was scratched until a precipitate appeared). The precipitate was filtered off and dried. Yield: 1.3 g of compound 3 (melting point: 180° C.).

Compound Identification

LCMS

For LCMS-characterization of the compounds of the present invention, the following procedure was used.

General Procedure A

The HPLC measurement was performed using an Alliance HT 2795 (Waters) system comprising a quaternary pump with degasser, an autosampler, a diode-array detector (DAD) and a column as specified in the respective methods below. Flow from the column was split to a MS detector. The MS detector was configured with an electrospray ionization source. The capillary needle voltage was 3 kV and the source temperature was maintained at 100° C. on the LCT (Time of Flight-Z-spray mass spectrometer from Waters). Nitrogen was used as the nebulizer gas. Data acquisition was performed with a Waters-Micromass MassLynx-Openlynx data system.

General Procedure B

The LC measurement was performed using a UPLC (Ultra Performance Liquid Chromatography) Acquity (Waters) system comprising a binary pump with degasser, an autosampler, a diode-array detector (DAD) and a column as specified in the respective methods below. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

LCMS Procedure 1

In addition to the general procedure A: Reversed phase HPLC was carried out on a Xterra-MS C18 column (5 µm, 4.6×150 mm) with a flow rate of 1.0 ml/min at a temperature of 30° C. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive ionization mode and 20 V for negative ionization mode. Mass spectra were acquired by scanning from 100 to 900 in 0.8 seconds using an interscan delay of 0.08 seconds.

LCMS Procedure 2

In addition to the general procedure B: Reversed phase UPLC was carried out on a Waters Acquity BEH (bridged ethylsiloxane/silica hybrid) C18 column (1.7 µm, 2.1×100 mm) with a flow rate of 0.35 ml/min at a temperature of 40° C. Two mobile phases (mobile phase A: 100% 7 mM ammonium acetate; mobile phase B: 100% acetonitrile) were employed to run a gradient condition from 75% A and 25% B (hold for 0.5 minutes) to 8% A and 92% B in 3.5 minutes, hold for 2 minutes and reequilibrated with initial conditions for 2 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

LCMS Procedure 3

In addition to the general procedure B: Reversed phase UPLC was carried out on a Waters Acquity BEH (bridged ethylsiloxane/silica hybrid) C18 column (1.7 μm, 2.1×100 mm) with a flow rate of 0.35 ml/min at a temperature of 40° C. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Chiral Phase HPLC

The Chiral phase HPLC measurement was performed using Waters HPLC system comprising two high pressure pumps (5115), a rheodyne injection valve, a single wavelength detector (2487) and a column.

Chiral phase HPLC analysis was carried out on a Chiralpak-AD column (10 μm, 4.6×250 mm) with a flow rate of 1 ml/min at room temperature. The mobile phase is composed of ethanol/methanol 50/50 to which 0.3% isopropylamine was added. The analysis was performed using isocratic conditions until complete elution. The detection was monitored at 254 nm. (UV-detector).

| Comp. Nr. | LCMS $R_t$ | $(MH)^+$ | Procedure | Chiral Phase HPLC Analysis (e.e.) |
|---|---|---|---|---|
| 1 (B1) | 8.77 | 413 | 1 | 100% |
| 2 | 8.77 | 413 | 1 | 100% |
| 1 (B2) | 3.17 | 413 | 2 | 99.7% |
| 3 | 3.49 | 413 | 3 | 99.2% |

In the table above, 'e.e.' means 'enantiomeric excess' and the retention times ($R_t$) are reported in minutes.

Comp. Nr. 1 (B1) shows the analytical data that was measured when compound 1 was prepared according to the method described in example B1. Comp. Nr. 1 (B2) shows the analytical data that was measured when compound 1 was prepared according to the method described in example B2.

Optical Rotation

The optical rotation was measured using a polarimeter. $[\alpha]_D^{20}$ indicates the optical rotation measured with light at the wavelength of the D-line of sodium (589 nm) at a temperature of 20° C. The cell pathlength is 1 dm. Behind the actual value the concentration and solvent of the solution which was used to measure the optical rotation are mentioned.

| Comp. Nr. | $[\alpha]_D^{20}$ | concentration | solvent |
|---|---|---|---|
| 1 (B1) | −44.44° | C = 10.17 mg/2 ml (0.5085 w/v %) | DMF |
| 2 | +41.88° | C = 10.65 mg/2 ml (0.5325 w/v %) | DMF |
| 1 (B2) | −47.41° | C = 5.40 mg/2 ml (0.2700 w/v %) | DMF |
| 3 | +10.14° | C = 9.27 mg/2 ml (0.4635 w/v %) | MeOH |

Comp. Nr. 1 (B1) shows the result for the optical rotation when compound 1 was prepared according to the method described in example B1. Comp. Nr. 1 (B2) shows the result for the optical rotation that was measured when compound 1 was prepared according to the method described in example B2.

C. Pharmacological Example

The capacity of the compounds to preserve p53 in A2780 cells was measured with the p53 enzyme linked immunosorbent assay. The p53 assay is a "sandwich" enzyme immunoassay employing two polyclonal antibodies. A polyclonal antibody, specific for the p53 protein, has been immobilized onto the surface of the plastic wells. Any p53 present in the sample to be assayed will bind to the capture antibody. The biotinylated detector polyclonal antibody also recognizes p53 protein, and will bind to any p53, which has been retained by the capture antibody. The detector antibody, in turn, is bond by horseradish peroxidase-conjugated streptavidin. The horseradish peroxidase catalyses the conversion of the chromogenic substrate o-phenylene diamine, the intensity of which is proportional to the amount of p53 protein bond to the plate. The colored reaction product is quantified using a spectrophotometer. Quantitation is achieved by the construction of a standard curve using known concentrations of purified recombinant HIS tagged p53 protein (see example C.1.).

C.1. p53 ELISA

A2780 cells (ATCC) were cultivated in RPMI 1640 supplemented with 10% fetal calf serum (FCS), 2 mM L-glutamine and gentamycin at 37° C. in a humidified incubator with 5% $CO_2$.

A2780 cells were seeded at 20.000 cells per well in a 96 well plate, cultured for 24 hours and treated with compound for 16 hours at 37° C. in a humidified incubator. After incubation, the cells were washed once with phosphate-buffered saline and 30 μl, per well, low salt RIPA buffer (20 mM tris, pH7.0, 0.5 mM EDTA, 1% Nonidet P40, 0.5% DOC, 0.05% SDS, 1 mM PMSF, 1 μg/ml aprotinin and 0.5 μ/ml leupeptin) was added. Plates were placed on ice for 30 minutes to complete the lysis. p53 protein was detected in de lysates by using the sandwich ELISA, described below.

High binding polystyrene EIA/RIA 96 well plates (Costar 9018) were coated with the capture antibody pAb1801 (Abcam ab28-100) at a concentration of 1 μg/ml in coating buffer (0.1 M $NaHCO_3$ pH8.2), 50 μl per well. The antibody was allowed to adhere overnight at 4° C. Coated plates were washed once with phosphate-buffered saline (PBS)/0.05% Tween 20 and 300 μl of blocking buffer (PBS, 1% bovine serum albumins (BSA)) was added, for an incubation period of 2 hours at room temperature. Dilutions of purified recombinant HIS tagged p53 protein, ranging from 3-200 ng/ml, were made in blocking buffer and used as standards.

Plates were washed twice with PBS/0.05% Tween 20 and blocking buffer or standards were added at 80 μl/well. To the standards, 20 μl of lysis buffer was added. The samples were added to the other wells at 20 µl lysate/well. After an overnight incubation at 4° C., plates were washed twice with PBS/0.05% Tween 20. Aliquots of 100 µl secondary polyclonal antibody p53(FL-393) (Tebubio, sc-6243) at a concentration of 1 µg/ml in blocking buffer were added to each well and allowed to adhere for 2 hours at room temperature. Plates were washed three times with PBS/0.05% Tween 20. Detection antibody anti-rabbit HRP (sc-2004, Tebubio) at 0.04 µg/ml in PBS/1% BSA was added and incubated for 1 hour at room temperature. Plates were washed three times with PBS/0.05% Tween 20 and 100 µl of substrate buffer was added (substrate buffer was prepared shortly before use by adding 1 tablet of 10 mg o-phenylene diamine (OPD) from Sigma and 125 µl 3% $H_2O_2$ to 25 ml OPD buffer: 35 mM citric acid, 66 mM $Na_2HPO_4$, pH5.6). After 5 to 10 minutes, colour reaction was stopped by adding 50 µl stop buffer (1 M $H_2SO_4$) per well. The absorbance at dual wavelengths of 490/655 nm was measured using a Biorad micro plate reader and the results were then analyzed.

For each experiment, controls (containing no drug) and a blank incubation (containing no cells or drugs) were run in parallel. The blank value was subtracted from all control and sample values. For each sample, the value of p53 (in absorbance units) was expressed as the percentage of the value for p53 present in the control. Percentage preservation higher than 140% was defined as significant. Herein the effects of test compounds are expressed as the lowest dose giving at least 140% of the value for p53 present in the control (LAD) (see table F-2 under example C.4). Also compound No. 3 was tested and showed an LAD of 1.00E-07.

In some of the experiments the assay was adapted for and used in 384-well culture plates C.2. P450 Assay The CYP P450 (*E. coli* expressed) proteins (3A4, 2D6, 2C9, 1A2 & 2C19) convert their specific substrates into a fluorescent molecule[1][2]. The fluorescent molecule is measured using a fluorescent plate reader. Compounds inhibiting the enzymatic reaction will result in a decrease of fluorescent signal (see example C.2).

Conversions Mediated by the Respective cDNA Expressed Cytochrome P450 Isoenzymes.

| Substrate | enzyme | fluorescent molecule |
|---|---|---|
| CEC | CYP1A2 → | CHC |
| MFC | CYP2C9 → | 7-HFC |
| CEC | CYP2C19 → | CHC |
| AMMC | CYP2D6 → | AMHC |
| BFC | CYP3A4 → | 7-HFC |
| DBF | CYP3A4 → | Fluorescein |
| 7-BQ | CYP3A4 → | Quinolinol |

Abbreviations:
CEC: 7-ethoxy-3-cyanocoumarin;
CHC: 3-cyano-7-hydroxycoumarin,
MFC: 7-Methoxy-4-trifluoromethyl coumarin;
7-HFC: 7-Hydroxy-trifluoromethyl coumarin,
CEC: 7-ethoxy-3-cyanocoumarin;
CHC: 3-cyano-7-hydroxycoumarin,
AMMC: 3-[2-(N,N-diethyl-N-methylamino)ethyl]-7-methoxy-4-methylcoumarin;
AHMC: 3-[2-(N,N-diethylamino)ethyl]-7-hydroxy-4-methylcoumarin hydrochloride,
BFC: 7-Benzyloxy-trifluoromethyl coumarin;
DBF: Dibenzylfluorescein,
7-BQ: Benzyloxyquinoline.

Cofactor Mix: (for all CYP Enzymes Except for CYP 2D6)

| | working solution | | final concentration |
|---|---|---|---|
| G-6-P | 8.25 mM | 25.10 mg | 3.3 mM |
| G-6-P-DH | 1 U/ml | 14.29 µl | 0.4 U/ml |
| 0.5M $MgCl_2 \cdot 6H_2O$ | 8.25 mM | 165.0 µl | 3.3 mM |
| NADP | 3.25 mM | 25.59 mg | 1.3 mM |
| dissolved in a 0.1M Na—K-phosphate buffer | | 10 ml | |

Abbreviations:
G-6-P: glucose-6-phosphate;
G-6-P-DH: glucose-6-phosphate-dehydrogenase.

Cofactor Mix: (for CYP2D6)

| | working solution | | final concentration |
|---|---|---|---|
| G-6-P | 1.025 mM | 3.12 mg | 0.41 mM |
| G-6-P-DH | 1 U/ml | 14.29 µl | 0.4 U/ml |
| 0.5M $MgCl_2 \cdot 6H_2O$ | 1.025 mM | 20.5 µl | 0.41 mM |
| NADP | 20.5 µM | 0.161 mg | 8.2 µM |
| dissolve in a 0.1M Na—K-phosphate buffer | | 10 ml | |

CYP P450 Enzyme Solutions:

| CYP1A2: | (CEC) | final concentration 5 pmol P450/ml |
|---|---|---|
| CYP2C9: | (MFC) | final concentration 60 pmol P450/ml |
| CYP2C19: | (CEC) | final concentration 2.5 pmol P450/ml |
| CYP2D6: | (AMMC) | final concentration 42 pmol P450/ml |
| CYP3A4: | (BFC) | final concentration 83 pmol P450/ml |
| | (DBF) | final concentration 5 pmol P450/ml |
| | (7-BQ) | final concentration 20 pmol P450/ml |

All these CYP enzymes were dissolved in 0.01 M Na—K-phosphate buffer+1.15% KCl, and kept on ice until use. The CYP P450 enzymes were stored at −80° C.

Compound and Reference Inhibitor Dilution:

Compounds and reference inhibitors were delivered to the department as a 5 mM solution in DMSO. A working solution of $5.10^{-4}$M was made by serial dilution using acetonitrile. The final compound concentration was $10^{-5}$M for the primary screen, and the final solvent concentration 2%. After a primary screen at a concentration of $10^{-5}$M, the $IC_{50}$ values of selected potent inhibitors were tested at a concentration range of $3.10^{-9}$-$10^{-5}$ M. In the primary screen, all compounds were tested in triplicate. Reference inhibitors were tested at a concentration range of $10^{-9}$-$10^{-4}$ M.

Reference Inhibitors:

| Furafylline: | (Ultra Fine Chemicals) | for CYP1A2 |
|---|---|---|
| Sulfaphenazole: | in house | for CYP2C9 |
| Tranylcypromine: | in house | for CYP2C19 |
| Quinidine: | in house | for CYP2D6 |
| Ketoconazole: | in house | for CYP3A4 |

Substrate Solutions:

| | | | |
|---|---|---|---|
| CEC | (CYP1A2 substrate) | 6.25 µl 20 mM CEC solution/5 ml total volume | 5 µM |
| MFC | (CYP2C9 substrate) | 200 µl 25 mM MFC solution/5 ml total volume | 200 µM |
| CEC | (CYP2C19 substrate) | 31.25 µl 20 mM CEC solution/5 ml total volume | 25 µM |
| AMMC | (CYP2D6 substrate) | 150 µl 0.5 mM AMMC solution/5 ml total volume | 3 µM |
| BFC | (CYP3A4 substrate) | 750 µl 5 mM BFC solution/5 ml total volume | 150 µM |
| DBF | (CYP3A4 substrate) | 12.5 µl 2 mM DBF solution/5 ml total volume | 1 µM |
| 7-BQ | (CYP3A4 substrate) | 60 µl 25 mM 7-BQ solution/5 ml total volume | 60 µM |

The substrate stock solutions were dissolved in acetonitrile, and stored at −20° C. The final working solution was dissolved in 0.1 M Na—K-phosphate buffer pH 7.4, and this solution was always prepared fresh before starting the assay.

Data Analysis

Plate preparation, data linking, data analysis, results validation & approval and data upload were semi-automatically performed by the Lexis-Laplace software (Laplace-DLM-RVAM)

The formula used in the calculations are:

% activity=(100/(avg positive control−avg negative control))×(avg sample−avg negative control).

% inhibition=100−% activity

When calculated, the $IC_{50}$ value was automatically generated by graphical extrapolation in RVAM, based on the intersection with the 50% of control axis.

Method

The assay was performed in a black 96 well Costar plate. Per well the assay comprises: 40 µl CYP P450 enzyme solution (in the negative control samples 40 µl of 0.1M Na—K-phosphate buffer pH 7.4 without enzyme was added); 40 µl cofactor mix; 2 µl compound or reference inhibitor for negative control samples or solvent for positive control samples. After 5 min preincubation at 37° C. in a shaking incubator, 20 µl substrate solution was added. The plates were incubated at 37° C. for 10 min (CYP3A4/DBF), 15 min (CYP1A2), 30 min (CYP2C9, CYP3A4/BFC and CYP3A4/7-BQ & CYP2C19) and 45 min (CYP2D6). The reaction was stopped by addition of 200 µl acetonitrile. For CYP3A4/DBF the reaction was stopped by addition of 200 µl 2M NaOH. For CYP3A4/7-BQ the reaction was stopped by addition of 40 µl Tris/acetonitrile (1:5) (V:V, followed by a 10 minute centrifugation at 2000 rpm. The fluorescent signal was detected by a fluorescent Victor2 (Wallac) or Fluoroskan (Labsystems) reader. The excitation and emission wavelength for the different enzymes and their specific substrate are mentioned in the Table 1, results obtained with compound No. 1 and compound No. 2 can be found in Table F-2 under example C.4.

TABLE 1

Excitation and emission wavelengths

| Enzyme | Substrate | Excitation wavelength | Emission wavelength |
|---|---|---|---|
| CYP1A2 | CEC | 410 nm | 460 nm |
| CYP3A4 | BFC | 405 nm | 535 nm |
| CYP3A4 | DBF | 485 nm | 538 nm |
| CYP3A4 | 7-BQ | 405 nm | 535 nm |
| CYP2C9 | MFC | 405 nm | 535 nm |
| CYP2C19 | CEC | 410 nm | 460 nm |
| CYP2D6 | AMMC | 390 nm | 460 nm |

REFERENCES

[1] Microtiter Plate Assays for Inhibition of Human, Drug-Metabolizing Cytochromes P450 Charles L. Crespi, Vaughn P. Miller, Bruce W. Penman (Gentest) Analytical Biochemistry 248, 188-190 (1997) Article n° AB972145

[2] Novel High Throughput fluorescent P450 assays V. P. Miller, J. Ackermann, D. M. Stresser, C. L. Crespi Gentest Internet site.

C.3. Ro-4-1284 Antagonism in Mice[3,4,5]

The test is a modification of a procedure described by Colpaert et al. (1975).[3] Male NMRI mice (22±3 g) were housed in macrolon observation cages (L×W×H: 11×12×17 cm; n=3 per cage). At the start of the experiments immediately before test compound administration, the initial body temperature of the mice was measured with a precision of 0.1° C. by inserting the thermo-sensitive probe (1.0 mm diameter) of an electric thermometer (Comark) to a constant depth of 3 cm into the esophagus until a stable reading was obtained. The right eye pupil diameter was measured with a graduated microscope and expressed in 1/24 mm units. Fifteen min after test compound administration, the mice were challenged with Ro-4-1284 (10 mg/kg, s.c.). Ro-4-1284 is a reserpine-like vesicular monoamine transport (VMAT-2) inhibitor, which rapidly depletes secretory vesicles.[3,4] Fifteen, 30 and 60 min after challenge, the mice were scored for palpebral opening (0, 1, 2, 3, 4, 5) and locomotor activity (−1, 0, 1, 2, 3). At the 60-min interval, immediately after the scoring of overt behavior, the right eye pupil diameter and the esophageal temperature were measured again. Abnormal phenomena such as intensive sniffing, chewing, rearing, hyperemia, piloerection, salivation, tremors, convulsions and death were noted (the latter phenomena were also noted when occurring before Ro-4-1284 administration). Criteria for drug-induced effects: reversal of ptosis: palpebral opening score >1 at 15, 30 or 60 min (2.7, 0.5 and 0% false positive controls, respectively; n>350); induction of prostration: score −1 for locomotion at 15, 30 or 60 min (never observed in controls); reversal of hypomotility: score >0 for locomotion at 15, 30 and 60 min (2.2, 0.8 and 0% false positive controls, respectively); reversal of miosis: pupil diameter >5 units at 60 min (0.8% false positives); potentiation of hypothermia: temperature decrease (over the 1-h time interval)>9.0° C. (1.4% false positives); reversal of hypothermia: temperature decrease <3.0° C. (1.8% false positives).

According to the standard procedure, R0-4-1284 is injected 15 min following subcutaneous or oral administration and observations start 15 min later. Doses are initially given to 3 animals. When at least 2 out of the 3 animals show activity for at least one of the observations, the compound is considered active. In other cases, the compound is considered inactive at the particular time-route-dose regimen and classified as finished.

Compound No. 1 and compound No. 2 were each tested on 3 animals at a concentration of 80 mg/kg following oral administration and they did not show activity on any observation on any animal.

REFERENCES

[3] Colpaert, F. C., Lenaerts, F. M., Niemegeers, C. J. E., Janssen, P. A. J.: "A critical study on Ro-4-1284 antagonism in mice.", Arch. Int. Pharmacodyn. 215 40-90 (1975).
[4] Colzi, A., D'Agostini, R., Cesura, A. M., Borroni, E., Da Prada, M.: "Monoamine oxidase-A inhibitors and dopamine metabolism in rat caudatus: evidence that an increased cytosolic level of dopamine displaces reversible monoamine oxidase-A inhibitors in vivo.", J. Pharmacol. Exp. Ther. 265 103-111 (1993).
[5] Filinger, E. J.: "Effect of a reserpine-like agent on the release and metabolism of [$^3$H]NA in cell bodies and terminals.", Gen. Pharmacol. 25 1039-1043 (1994).

C.4. Comparative Data with Compounds Present in EP1809622

Surprisingly, the present compounds show excellent in-vitro activity, which is combined with lower affinity for P450 enzymes and no in vivo drug induced neurological effects. Even more surprisingly, the S-enantiomer of the invention (Compound No. 1), when tested in p53 ELISA (see example C.1.), has an activity higher than the activity obtained with the structurally closest compounds of the prior art, of which the most active one is an R-enantiomer (Compound No. 229 of EP1809622) (see Table F-2).

Table F-2 gives data for the compounds of the present invention when compared with compounds of the prior art. As described above five P450 enzymes were tested, one of them on three different substrates (thus seven tests in total). In the table is indicated on how many P450 tests a compound showed an inhibitory activity with an $IC_{50} < 1.00E-06$.

TABLE F-2

| | Comparative data | | | |
|---|---|---|---|---|
| compound | U87MG p53-elisa LAD | A2780 p53-elisa LAD | P450 effects $IC_{50}$ | drug induced neurological side effects |
| 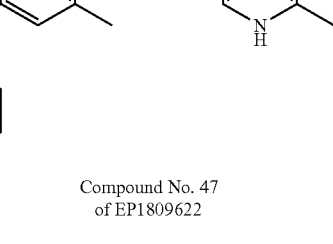<br>Compound No. 47 of EP1809622 | 1.00E-05 | 3.00E-06 | 7 times < 1.00E-06 | yes |
| 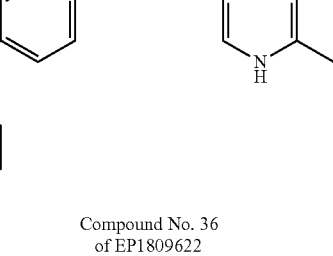<br>Compound No. 36 of EP1809622 | 3.00E-06 | 1.00E-06 | 3 times < 1.00E-06 | yes |
| 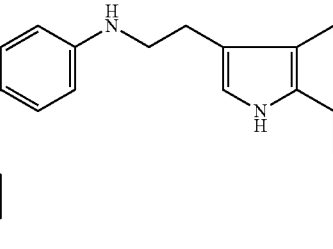<br>Compound No. 197 of EP1809622 | 1.00E-06 | 3.00E-07 | 7 times < 1.00E-06 | yes |

TABLE F-2-continued

Comparative data

| compound | U87MG p53-elisa LAD | A2780 p53-elisa LAD | P450 effects IC$_{50}$ | drug induced neurological side effects |
|---|---|---|---|---|
| 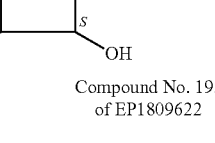<br>Compound No. 195 of EP1809622 | 1.00E-06 | 1.00E-07 | 0 times < 1.00E-06 | yes |
| 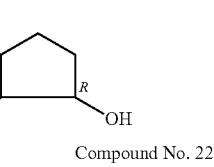<br>Compound No. 229 of EP1809622 | 1.00E-07 | 3.00E-07 | 0 times < 1.00E-06 | yes |
| 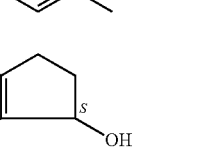<br>compound No. 1 | | 3.00E-08 | 0 times < 1.00E-06 | No |
| 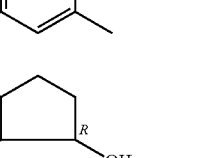<br>Compound No. 2 | | 1.00E-07 | 0 times < 1.00E-06 | No |

The U87MG p53-elisa as described in EP1809622 was no longer used for the present invention, since the A2780 p53-elisa displayed better sensitivity.

C.5. In Vivo Anti Tumour Effects

Co No. 1 showed potent inhibition in growth of the subcutaneously (s.c.) injected human U87 gliomoblastoma xenograft tumors in NMRI Nude mice. In the pre-established U87 gliomoblastoma xenograft tumors (~200-300 mm³ tumor volume), complete tumor growth inhibition and regression was observed after oral administration for 21 days at both 10 and 20 mg/kg (FIG. 7). The minimal efficacious dose (according to the NCI standard) in this model was 5 mg/kg. Also compound No. 2 showed in vivo antitumoral activity.

NCI Standard Reference

Bissery, M-C., and Chabot, G. G. History and new development of screening and evaluation methods of anticancer drugs used in vivo and in vitro. Bull. Cancer. 1991, 78: 587-602.

Animal Model:

Immuno-deficient (athymic) male NMRI Nude (Nu/Nu) mice (20-25 g were obtained from Janvier, France) were used for theses studies. Initial weight was approximately 23 to 34 g. All animals were maintained under SPF "full barrier" conditions with free access to food and water. Mice were group housed under a 12-h light:dark cycle (lights on at 06:00 h) at a temperature of 19 to 22° C. and 35 to 40% humidity in Techniplast type-3 IVC cages. Mice were fed a standard Laboratory chow. All experiments were carried out in accordance with the European Communities Council Directives (86/609/EEC) and were approved by the local ethical committee. For an established tumor xenograft model (tumor volume ~200 mm$^3$), mice were randomized according to tumor volumes, with 10 to 14 mice per treatment group.

Test System:

The human U87 glioma tumor cell line was derived from a 44 year old female Caucasian patient. Cells were cultured at 37° C. in a humidified atmosphere (5% $CO_2$, 95% air), in DMEM medium supplemented with 2 mM L-glutamine, 2.0 mM sodium pyruvate, 25 units/ml penicillin/25 µg/ml streptomycin and 10% fetal bovine serum. Cells were maintained as cell monolayer cultures, being passaged twice weekly at $3 \times 10^6$ cells per T175 flask using the following procedure. Briefly cells were washed with PBS (without $Mg^{2+}$, $Ca^{2+}$), before addition of trypsin-EDTA to the culture flasks. After detachment of cells the trypsin-EDTA was inactivated by addition of complete medium. Cell suspension was then transferred to 50 ml Falcon tube and centrifuged for 3 min at 1200 rpm. Medium was aspirated, with the cells being re-suspended in an appropriate volume of complete medium. The cells were counted in a haemocytometer and their viability was assessed by 0.25% trypan blue exclusion. An appropriate volume of cell suspension was then added to either a new T175 culture flask(s) or roller bottle containing fresh medium. For large scale-up growth of U87 tumor cells, an appropriate number of roller bottles were seeded with 0.5 to $1 \times 10^7$ cells 1 week prior to inoculation of mice. The medium was changed twice during this period, with the last change being the day prior to cell injection. Cells were collected as described above, with the exception that after centrifugation, the cells were re-suspended in cold (4° C.) serum-free medium. Mice were injected in the inguinal region with $1 \times 10^7$ cells total in a 200 µl volume.

Study Design:

Human U87 glioma cells were injected directly into the inguinal region of the male NMRI Nude mice ($1 \times 10^7$ cells/200 µl/animal) on day 0 (D0). On day 8 (D8), when tumor volume had reached an approximate average of 200 mm$^3$, mice were randomized according to tumor volume, with 10 to 14 mice per treatment group. Mice were then treated once daily (QD) with either vehicle (10% HP-β-CD) or vehicle containing Compound No. 1 by gavage (p.o.) administered in a volume of 10 ml/kg body weight for 21 days. Tumor size and body weights were measured twice weekly, with mice monitored daily for clinical signs of toxicity for the duration of the treatment. Clinical signs of toxicity included (but not limited to), persistent anorexia or dehydration, posture, moribund, lethargy, hypothermia and/or laboured respiration (according to the UKCCCR guidelines for welfare of animals in experimental neoplasia (The UKCCCR (UK Coordinating Committee on Cancer Research) guidelines for the welfare of animals in experimental neoplasia (July 1997); and Workman, P. et al. UKCCCR guideline. *Br. J. Cancer.* 1998, 77: 1-10).

Data Analysis:

For each individual animal, body weight and tumor size [using the commonly accepted formula: Tumor Volume (mm$^3$)=(a×b$^2$/2); where 'a' represents the length, and 'b' the width of the tumor as determined by caliper measurements], were monitored twice weekly throughout the study. A sustained body weight loss greater than 15% of the initial body weight is considered as clinical toxicity, with the animal removed from the study and sacrificed. Time-course of tumor growth was expressed as median values, or normalized to initial tumor volume on the day treatment started and expressed as mean±standard error of the mean (SEM). For pre-established tumors, relative tumor volumes were calculated for each mouse (treated tumor volume/tumor volume on day 0) and expressed as mean±SEM for each treatment group. Twenty-four hours post last treatment, animals were sacrificed, tumors excised and weighed. Statistical significance was indicated by one-sided p-values from Wilcoxon-Mann-Whitney analysis (Wilcoxon rank sum test) and $p<0.05$ was considered as statistically significant. Treatment/control (T/C) ratios were calculated based on final relative tumor volumes, using the NCI criteria. Results are given in FIG. 7.

D. Preparation of Compound No. 1 Crystalline Form I and II

Four compound No. 1 batches made following the procedure under example B1 were characterised using following physicochemical techniques: Infrared Spectrometry (IR), Differential Scanning calorimetry (DSC) and Powder X-ray Diffraction (XRPD) and indicated that at least 2 polymorphic forms exist (see Table 2).

TABLE 2

Physical properties of batches of compound No. 1

| Batch | DSC Melting Point (° C.) | DSC Melting Enthalpy ΔH (J/g) | IR | XRPD |
|---|---|---|---|---|
| 1 | 186.5 | 83 | Form II | Form II |
| 2 | 185.6 | 82 | Form II | Form II |
| 3 | 191.9 | 113 | Form I | Form I |
| 4 | 192.1 | 122 | Form I | Form I |

Form I was denoted as a crystalline, non-hygroscopic solid that melts at approximately 192° C. Form II was described as a crystalline solid with a melting point at approximately 186° C. Typical XRPD patterns, IR spectra, and DSC scans for the 2 solid state forms (batch 2 and 4) of Co No. 1 are shown in FIGS. 1 to 6.

The crystallographic stability of Form I of compound No. 1 was studied according to the following procedure:

after storage of the compound in open conditions for a period of six weeks at room temperature (RT) under <5%, 56% and 75% relative humidity (RH), 50° C. and 40° C./75% RH., the samples were analyzed with thermogravimetry (TGA), differential scanning calorimetry (DSC), X-ray powder diffraction (XRPD) and infrared spectroscopy (IR).

The results of the test are reported in the following table. Form I is crystallographically stable.

|  | condition | TGA <175° C. | TGA <225° C. | XRD | IR | DSC Max (° C.) | DSC ΔH (J/g) | App |
|---|---|---|---|---|---|---|---|---|
| Form I | 0 days | 0.05 | 0.19 | Cryst., Ref | Cryst., Ref | 192.1 | 122 | brown-grey |
|  | RT/<5% RH | 0.00 | 0.31 | ~Ref | ~Ref | 191.7 | 125 | brown-grey |
|  | RT/56% RH | 0.15 | 0.20 | ~Ref | ~Ref | 191.8 | 108 | brown-grey |
|  | RT/75 % RH | 0.14 | 0.25 | ~Ref | ~Ref | 191.7 | 112 | brown-grey |
|  | 50° C. | 0.00 | 0.20 | ~Ref | ~Ref | 191.6 | 122 | brown-grey |
|  | 40° C./75% RH | 0.06 | 0.19 | ~Ref | ~Ref | 191.7 | 123 | brown-grey |

~Ref: identical with reference
Cryst.: crystalline

The chemical stability of Form I of compound No. 1 was studied according to the following procedure:

Form I was stored in different open conditions for periods of 1, 4 and 8 weeks. These conditions are 40° C./75% RH, 50° C., RT/<5% RH, RT/56% RH, RT/75% RH and 0.3 da ICH light.

The compounds were analyzed after storage by HPLC and by visual inspection.

The results of the tests are reported in the following table. Form I is chemically stable in all investigated conditions.

|  | condition | HPLC Sum of impurities 1 week | 4 weeks | 8 weeks | Appearance 1 week | 4 weeks | 8 weeks |
|---|---|---|---|---|---|---|---|
| Form I | Reference | 0.23 | — | — | brown-grey | — | — |
|  | 0.3da ICH light | 0.18 | — | — | brown-grey | — | — |
|  | 40° C./75% RH | 0.13 | 0.14 | 0.20 | brown-grey | brown-grey | brown-grey |
|  | 50° C. | 0.28 | 0.14 | 0.24 | brown-grey | brown-grey | brown-grey |
|  | RT/<5% RH | — | 0.19 | 0.24 | — | brown-grey | brown-grey |
|  | RT/56% RH | — | 0.22 | 0.24 | — | brown-grey | brown-grey |
|  | RT/75% RH | — | 0.20 | 0.18 | — | brown-grey | brown-grey |

D.1. Automated Polymorph Screen

Saturated/concentrated solutions of compound No. 1 (batch 4) were prepared at 50° C. in 13 solvents (water, methanol, ethanol, 2-propanol, acetone, acetonitrile, toluene, tetrahydrofuran, dichloromethane, 2-butanone, ethyl acetate, dimethylformamide, 1-methoxy-2-propanol). To ensure that saturation was achieved, drug substance was added to each solvent system until the solid no longer dissolved. After equilibrating the solutions overnight at 50° C., a portion of each solution was filtered and the filtrates were set aside for use in the automated polymorph screen.

Using a Gilson 215 liquid handler, the automated polymorph screen samples were prepared in a well plate containing 1.0 mL glass insert vials. The filtrates from the 13 concentrated/saturated compound No. 1 solutions were dispensed at 50° C. as a 13×13 solvent array consisting of 13 pure solvents and 78 binary solvent mixtures (50/50 v/v %). The total solution volume delivered to each well was 950 μL. After the dispensing step, the plate was sealed using a Teflon coated plate mat and left at room temperature over night. The plate seal was then removed and replaced with a pre-slit Teflon coated plate mat. The solvents were then allowed to evaporate slowly. Upon evaporation, the plate was placed under vacuum for 1 week. The solids were then analyzed by XRD and IR.

Of the 91 experiments performed for compound No. 1 in the automated polymorph screen, only 26 solvent combinations produced crystalline solids of varying morphology (see Table). Analysis of these solids by XRD and IR showed the solids to be Form I.

TABLE 3

Morphology of crystalline solids of form I

| Solvent Mixture | Morphology |
|---|---|
| Water/Methanol | Ultra fine needles |
| Water/Ethanol | Ultra fine needles |
| Water/2-Propanol | Ultra fine needles |
| Water/Acetone | Ultra fine needles |
| Water/Acetonitrile | Ultra fine needles |
| Water/THF | Ultra fine needles |
| Water/Dichloromethane | Ultra fine needles |
| Water/2-Butanone | Ultra fine needles |
| Water/Ethyl Acetate | Ultra fine needles |
| Water/1-Methoxy-2-Propanol | Ultra fine needles |
| Methanol | Fine needles |
| Methanol/Ethanol | Fine needles |
| Methanol/2-Propanol | Fine needles |
| Methanol/1-Methoxy-2-Propanol | Fine needles |
| Ethanol | Fine needles |
| Ethanol/2-Propanol | Fine needles |
| Ethanol/Acetonitrile | Fine needles |
| 2-Propanol | Ultra fine needles |
| Acetone/Acetonitrile | Large needles or Rods |
| Acetone/Toluene | Fine Needles |
| Acetone/Ethyl Acetate | Large Needles |
| Acetonitrile | Large Needles or Rods |
| Acetonitrile/2-Butanone | Rods |

TABLE 3-continued

Morphology of crystalline solids of form I

| Solvent Mixture | Morphology |
|---|---|
| 2-Butanone | Fine Needles |
| 2-Butanone/Ethyl Acetate | Fine Needles |
| Ethyl Acetate | Large Needles or Rods |

D.2. Slurry Conversion Experiment

Concentrated/saturated solutions of compound No. 1 drug substance were prepared at 50° C. in 13 different solvents (water, methanol, ethanol, 2-propanol, acetone, acetonitrile, toluene, tetrahydrofuran, dichloromethane, 2-butanone, ethyl acetate, dimethylformamide, 1-methoxy-2-propanol) to support the automated polymorph screen. After heating the solutions at 50° C. overnight, excess solid was observed to be present in the following solvents: ethyl acetate, 2-propanol, acetonitrile, toluene, water, ethanol, and methanol. The slurry solids were retrieved from their solvent systems, dried under an air stream, placed under vacuum at room temperature overnight, and then analyzed for slurry conversion using XRD.

No form conversion was observed for the compound No. 1 drug substance (Form I) when slurried in various solvents at moderate temperatures (50° C.) over short periods of time (24 hours).

E. Composition Example

Film-Coated Tablets

Preparation of Tablet Core

A mixture of 100 g of a compound of formula (I), 570 g lactose and 200 g starch is mixed well and thereafter humidified with a solution of 5 g sodium dodecyl sulphate and 10 g polyvinyl-pyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of a compound of formula (I).

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol, 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

The invention claimed is:

1. A compound of formula (I),

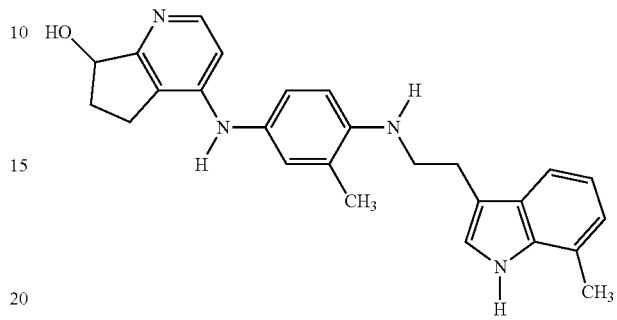

(I)

a N-oxide form, an addition salt, a stereochemically isomeric form or a solvate thereof.

2. A compound according to claim 1 wherein the compound is compound No. 1 or compound No. 2

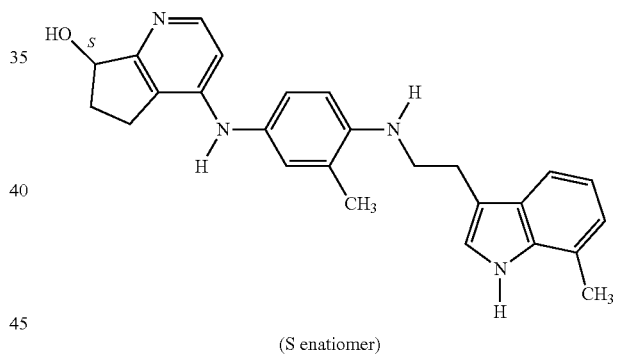

Compound No. 1

(S enatiomer)

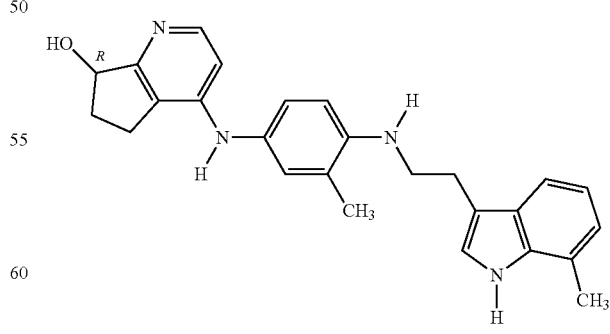

Compound No. 2

(R enantiomer)

3. A compound according to claim 1 wherein the compound is compound No. 1 or compound No. 3

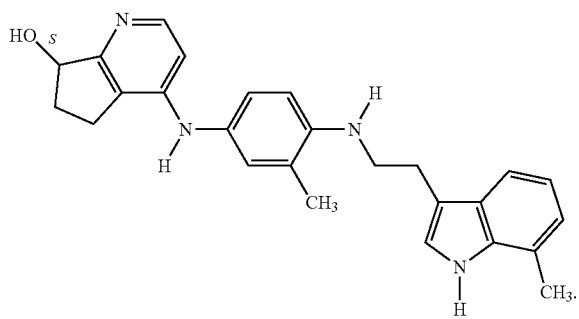

Compound No. 1 (S-enantiomer)
Compound No. 3 (S-enantiomer; HCl-salt)

4. A compound according to claim 1 wherein the compound is compound No. 1

Compound No. 1

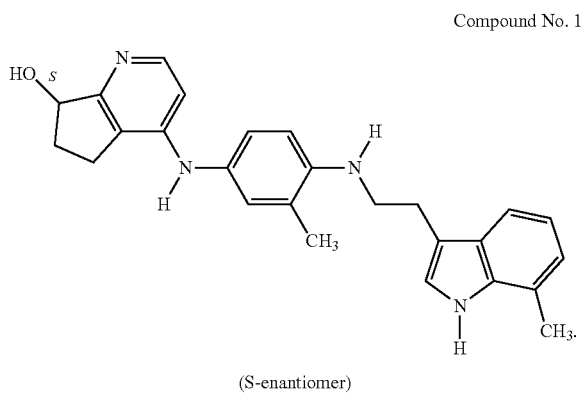

(S-enantiomer)

5. A crystalline form of compound No. 1 according to claim 4.

6. A crystalline form according to claim 5, wherein form is essentially pure.

7. The crystalline form according to claim 5 or 6, wherein the crystalline form has any one or more of the following:
- a X-ray powder diffraction (XRPD) pattern comprising diffraction peaks at two-theta positions of 6.4°±0.2°, 12.8°±0.2°, 15.2°±0.2° and 17.3°±0.2°;
- a XRPD pattern comprising diffraction peaks at two-theta positions as depicted in FIG. 2;
- an infrared spectrometry (IR) micro attenuated reflectance spectrum with absorption bands at 3403±1 cm$^{-1}$, 3150±1 cm$^{-1}$, 1595±1 cm$^{-1}$, 1517±1 cm$^{-1}$, 1320±1 cm$^{-1}$, 1165±1 cm$^{-1}$, 1071±1 cm$^{-1}$, 882±1 cm$^{-1}$, 819±1 cm$^{-1}$, 781±1 cm$^{-1}$ and 733±1 cm$^{-1}$;
- an IR spectrum comprising peaks at absorption bands (cm$^{-1}$) as depicted in FIG. 1;
- a differential scanning calorimetry (DSC) curve with an endothermic peak at about 191.9° C.

8. A crystalline form according to claim 5 or 6, wherein the crystalline form has any one or more of the following:
- a X-ray powder diffraction (XRPD) pattern comprising diffraction peaks at two-theta positions of 8.2°±0.2°, 12.5°±0.2°, 18.2°±0.2°, 21.9°±0.2° and 27.5°±0.2°;
- a XRPD pattern comprising diffraction peaks at two-theta positions as depicted in FIG. 5;
- an infrared spectrometry (IR) micro attenuated reflectance spectrum with absorption bands at 3411±1 cm$^{-1}$, 3352±1 cm$^{-1}$, 1600, 1508, 1480, 1327, 1171, 1079, 810, 770 and 743 cm$^{-1}$±1 cm$^{-1}$;
- an IR spectrum comprising peaks at absorption bands (cm$^{-1}$) as depicted in FIG. 4;
- a differential scanning calorimetry (DSC) curve with an endothermic peak at about 185.6° C.

9. A pharmaceutical composition comprising pharmaceutically acceptable carriers and as an active ingredient a therapeutically effective amount of a compound as claimed in claim 1.

* * * * *